United States Patent [19]

Frei et al.

[11] Patent Number: 5,627,215
[45] Date of Patent: May 6, 1997

[54] UNSATURATE AMINO COMPOUNDS FOR USE AS ANTICANCER AND ANTIPROTOZOIC AGENT

[75] Inventors: Jörg Frei, Hölstein; Jaroslav Stanek, Arlesheim, both of Switzerland

[73] Assignee: Ciba-Geigy Corporation, Tarrytown, N.Y.

[21] Appl. No.: 505,329

[22] PCT Filed: Dec. 14, 1994

[86] PCT No.: PCT/EP94/04230

§ 371 Date: Aug. 18, 1995

§ 102(e) Date: Aug. 18, 1995

[87] PCT Pub. No.: WO95/18091

PCT Pub. Date: Jul. 6, 1995

[30] Foreign Application Priority Data

Dec. 27, 1993 [CH] Switzerland ............................. 3876/93

[51] Int. Cl.$^6$ .................. A61K 31/13; C07C 211/22; C07C 211/25

[52] U.S. Cl. .................. 514/674; 514/659; 514/660; 564/512; 564/455; 564/457; 564/461; 564/462

[58] Field of Search ................... 564/512, 461, 564/462, 455; 514/674, 659, 660

[56] References Cited

U.S. PATENT DOCUMENTS

| | | | |
|---|---|---|---|
| 2,991,290 | 7/1961 | Shapiro et al. | 564/123 |
| 4,278,605 | 7/1981 | Murdock et al. | 424/330 |

FOREIGN PATENT DOCUMENTS

| | | |
|---|---|---|
| 0270349 | 6/1988 | European Pat. Off. . |
| 0277635 | 8/1988 | European Pat. Off. . |
| 0349224 | 1/1990 | European Pat. Off. . |
| 0353752 | 2/1990 | European Pat. Off. . |
| 2118405 | 10/1977 | Japan . |
| 9302045 | 2/1993 | WIPO . |

OTHER PUBLICATIONS

Weinstock, L. T. et al. "Synthesis of New Polyamine Derivatives for Cancer Chemotherapeutic Studies" Journal of Pharmaceutical Studies (70):956–959 (1981).

Bergeron, R. J. et al. "Synthetic Polyamine Analogs as Antineoplastics" Journal of Medicinal Chemistry (31):1183–1190 (1988).

Nagarajan, S. et al "Chemistry of Naturally Occuring Polyamines." Journal of Organic Chemistry (52):5044–5046 (1987).

Porter, Carl et al. "Biological Properties of $N^4$-and $N^1,N^8$-Spermidine Derivatives in Cultured L1210 Leukemia Cells" Cancer Research (45):2050–2057 (1985).

Saab, Nada et al "Synthesis and Evaluation of Unsymmetrically Substituted Polyamine Analogues as Modulators of Human Spermidine/Spermine–$N^1$–Acetyltransferase (SSAT) and as Potential Antitumor Agents[1]" J. Med Chem (36) 2998–3004 (1993).

Pegg et al. "Role of Unsaturated Derivatives of Spermidine as Substrates for Spermine Synthase and in Supporting Growth of SV–3T3 Cells" Biochem (274):167–171, (1991).

Bernacki, Grace. "Antitumor Activity of N,N'-Bis(ethyl)spermine Homologues Against Human MALME–3 Melanoma Xenografts[1]" Cancer Research (52) 2424–2430 (1992).

Porter, Carl et al. "Relative Abilities of Bis(ethyl) Derivatives of Putrescine, Spermidine, and Spermine to Regulate Polyamine Biosynthesis and Inhibit L1210 Leukemia Cell Growth[1]" Cancer Research (47) 2821–2825 (1987).

Okada Jutaro, et al "Syntheses of N–(2–Hexahydropyrimidinoethyl)proplonanilides[1])" Chem. Pharm. Bull. (28):3310 (1980).

Primary Examiner—José G. Dees
Assistant Examiner—Deborah Lambkin
Attorney, Agent, or Firm—Karen G. Kaiser

[57] ABSTRACT

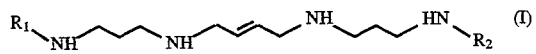

The invention relates to compounds of formula (I), $R_1$ and $R_2$, each independently of the other, are selected from lower alkyl that is unsubstituted or substituted by one or more fluorine atoms which are not linked to the carbon atom of $R_1$ or $R_2$ bonding the nitrogen; from lower alkenyl wherein the double bond does not originate from the carbon atom that is bonded to a nitrogen bonding $R_1$ or $R_2$; from lower alkynyl wherein the triple bond does not originate from the carbon atom that is bonded to a nitrogen bonding $R_1$ or $R_2$; from cycloalkyl; and from cycloalkyl-lower alkyl; with the proviso that not more than one of the two radicals $R_1$ and $R_2$ is methyl; or salts thereof. The mentioned compounds are pharmacologically active against disorders that are responsive to a reduction in intracellular polyamines, such as tumours or protozoal diseases.

11 Claims, No Drawings

UNSATURATE AMINO COMPOUNDS FOR USE AS ANTICANCER AND ANTIPROTOZOIC AGENT

This application is filed under 35 U.S.C. §371 as a national phase application of PCT/EP94/04230, filed Dec. 14, 1994, which was based on Switzerland Application No. 3876/93-9, filed Dec. 27, 1993.

The invention relates to $N^1,N^{14}$-disubstituted tetraazatetradec-7-enes and their salts, to processes for the preparation of those compounds, to pharmaceutical compositions comprising those compounds, and to the use of those compounds in the therapeutic treatment of the human or animal body or in the preparation of pharmaceutical compositions.

Polyamines, for example spermine, spermidine and analogues thereof, have for some time been the subject of intensive investigation as regards their biological properties, especially as regards proliferative processes. An early finding has been that higher levels of polyamines are to be found in cells that are dividing, for example in cancer cells, than in cells that are stable.

Such phenomenological observations have led to the conclusion that polyamines are necessary for cell proliferation.

The concept of influencing the polyamine level in cells has therefore been made use of in chemotherapy, for example of cancerous diseases.

Surprisingly, it has now been found that the compounds of the present invention have especially valuable properties that can be used pharmacologically.

The compounds according to the invention are compounds of formula I

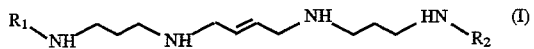

wherein $R_1$ and $R_2$, each independently of the other, are selected from lower alkyl that is unsubstituted or substituted by one or more fluorine atoms which are not linked to the carbon atom of $R_1$ or $R_2$ bonding the nitrogen; from lower alkenyl wherein the double bond does not originate from the carbon atom that is bonded to a nitrogen bonding $R_1$ or $R_2$; from lower alkynyl wherein the triple bond does not originate from the carbon atom that is bonded to a nitrogen bonding $R_1$ or $R_2$; from cycloalkyl; and from cycloalkyl-lower alkyl; with the proviso that not more than one of the two radicals $R_1$ and $R_2$ is methyl; or salts thereof.

Within the context of the present Application, the general terms used hereinbefore and hereinafter have preferably the following meanings:

Lower alkyl has especially up to a maximum of 7 carbon atoms, is branched or unbranched and is preferably methyl or especially $C_2$–$C_7$alkyl, such as ethyl, n-propyl, isopropyl, n-butyl, isobutyl, sec-butyl, tert-butyl, n-pentyl, neopentyl, n-hexyl or n-heptyl, especially methyl or more especially $C_2$–$C_4$alkyl, such as ethyl, n-propyl, isopropyl, n-butyl, sec-butyl or isobutyl, with ethyl and propyl, such as n-propyl, being especially preferred.

Those radicals are preferably unsubstituted but may also be substituted by one or more, preferably up to three, fluorine atoms, for example as in 2,2,2-trifluoroethyl. The fluorine atom is not bonded to the carbon atom in $R_1$ or $R_2$ that is bonded to the nitrogen in formula I.

Lower alkenyl has especially from 3 to 7, preferably 3 or 4, carbon atoms and is, for example, allyl or crotyl.

Lower alkynyl has especially from 3 to 7, preferably 3 or 4, carbon atoms and is, for example, propyn-2-yl or 2-butyn-1-yl.

In lower alkenyl and lower alkynyl, an unsaturated bond must not originate from the carbon atom that is bonded to a nitrogen atom bonding $R_1$ or $R_2$, as unstable compounds are otherwise formed.

Cycloalkyl has preferably from 3 to 7, especially from 3 to 5, carbon atoms and is especially cyclopropyl or cyclobutyl.

Cycloalkyl-lower alkyl contains as cycloalkyl especially a radical having from 3 to 5 carbon atoms, especially cyclopropyl or also cyclobutyl, and as lower alkyl radical preferably a radical as defined above, especially $C_1$–$C_3$alkyl, for example methyl, ethyl, n-propyl or isopropyl, more especially $C_1$–$C_2$alkyl. Preference is given to 2-cyclopropylethyl, cyclobutyl-methyl or, especially, cyclopropylmethyl.

On account of their basic properties, salts of compounds of formula I are especially acid addition salts, but may also be mixed salts.

Salts are especially the pharmaceutically acceptable, that is to say non-toxic, salts of compounds of formula I, that is to say especially the corresponding acid addition salts with acid anions that are not toxic (at the dose in question).

Such salts are formed, for example, by compounds of formula I with inorganic acids, for example hydrohalic acids, such as hydrochloric acid or hydrobromic acid, sulfuric acid or phosphoric acid, or with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, and also with amino acids, such as the 20 α-amino acids involved in the synthesis of proteins in nature, for example glutamic acid or aspartic acid, and also with methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Carbonates or hydrogen carbonates are also possible.

The mixed salts include, for example, salts of compounds of formula I with di- or tri-valent acids that have acid radicals having different dissociation constants, such as citric acid or phosphoric acid, where, for example, one or two protons of those acids have been replaced by cations, such as alkali metal cations, for example $Na^+$ or $K^+$, so that the corresponding salts still contain the corresponding cations as well as the compound of formula I and the corresponding acid anions.

The terms "compounds" and "salts" expressly include also individual compounds or individual salts.

For isolation or purification it is also possible to use pharmaceutically unacceptable salts, for example picrates or perchlorates. Only the pharmaceutically acceptable, non-toxic salts are used therapeutically, and those are therefore preferred.

The central double bond in the compounds of formula I is always in the E (=trans) form indicated. If asymmetric carbon atoms are present in one or both of the radicals $R_1$ and $R_2$, then the corresponding compounds may be in the form of isomeric mixtures, for example in the form of diastereoisomeric mixtures or racemates, or in pure form.

The compounds of the present invention have especially valuable pharmacological properties. In particular, it has surprisingly been found that the compounds of formula I effect a reduction in the intracellular concentrations (pool) of natural polyamines, such as, especially, putrescine, spermidine and spermine. This brings about a slowing down or suppression of cell divisions, especially a reduction in or cessation of the growth of growing (especially rapidly growing) tissues.

The reduction in the intracellular levels of polyamines, especially of putrescine, spermidine and/or spermine, is probably based primarily on the fact that the compounds of formula I reduce the activities of biosynthetic enzymes of polyamine biosynthesis, ornithine decarboxylase (ODC) and/or S-adenosylmethionine decarboxylase (SAMDC). Additionally or alternatively, the compounds of formula I can bring about an acceleration in the metabolic decomposition of natural polyamines; for example, induction of spermidine-spermine-acetyl-transferase, which in principle can even be super-induced, may be possible.

The reduction in the intracellular concentration of polyamines may be demonstrated, for example, as follows (see C. W. Porter et at., Cancer Res. 45, 2050–2057 (1985)):

Mouse ascites L1210 leukaemia cells are cultured (at 37° C.) in RPMI-1640 medium (which contains, per litre, 100 mg of $Ca(NO_3)_2$, 400 mg of KCl, 100 mg of $MgSO_4.7H_2O$, 6000 mg of NaCl, 2000 mg of $NaHCO_3$, 801 mg of $Na_2HPO_4$, 242 mg of L-Arg.HCl, 50 mg of L-Ash, 20 mg of L-Asp, 50 mg of L-Cys, 300 mg of L-Gln, 20 mg of L-Glu, 10 mg of Gly, 18.2 mg of L-His.HCl.$H_2O$, 20 mg of L-hydroxyproline, 50 mg of L-Leu, 40 mg of L-Lys.HCl, 15 mg of L-Met, 15 mg of L-Phe, 20 mg of L-Pro, 30 mg of L-Ser, 20 mg of L-Thr, 5 mg of L-Trp, 20 mg of L-Tyr, 20 mg of L-Vat, 1 mg of 1-aminobenzoic acid, 0.2 mg of biotin, 3 mg of choline chloride, 1 mg of folic acid, 35 mg of i-inositol, 1 mg of nicotinamide, 0.25 mg of pantothenoic acid calcium salt, 1 mg of pyridoxine.HCl, 0.2 mg of riboflavin, 1 mg of thiamine. HCl, 0.005 mg of vitamin $B_{12}$, 2000 mg of glucose, 1 mg of glutathione, and 5 mg of phenol red), which also contains 2 % 4-(2-hydroxyethyl)-1-piperazineethanesulfonic acid/3-(N-morpholino)propanesulfonic acid, 1 mM aminoguanidine and 10% NuSerum (Collaborative Research Inc., Lexington, Mass.). The cells are cultured under a humid 5% carbon dioxide atmosphere at 37° C. either in glass culture tubes (2 ml) or in 25 or 75 $cm^2$ tissue culture bottles in a total volume of 15 or 50 ml, respectively. The cultures are treated with the compounds of formula I or with 0.1 mM spermidine (controls: without corresponding compounds) during the logarithmic growth phase (0.5 to $1 \times 10^5$ cells/ml). The number of cells is measured by electronic particle counting (Model ZF Coulter Counter, Coulter Electronics, Hialeah, Fla.) and confirmed from time to time by haemocytometer measurements. The viability of the cells is measured by trypan blue exclusion measurement (0.5% in unbuffered 0.9% sodium chloride solution ).

For polyamine determination, the cell samples are washed twice in cold PBS (="Phosphate Buffered Saline"—contains per litre 8000 mg of NaCl, 200 mg of KCl, 1150 mg of $Na_2HPO_4.2H_2O$, 200 mg of $KH_2PO_4$, 100 mg of $MgCl_2.H_2O$, 200 mg of $MgSO_4.H_2O$ and $CaCl_2$; pH 7.2), and an aliquot of $10^7$ cells is removed for polyamine determination. The cells are formed into a pellet, and the PBS supernatant is removed carefully using a cotton wool swab. The pellet containing the cells is then maintained together with 0.5 ml of 0.6M perchloric acid for 30 minutes at 4° C. and is then centrifuged for 3 minutes at 12,000 g using a microcentrifuge. The supernatant is frozen at –20° C. until the HPLC analysis. For that purpose, the polyamines in a 50 µl sample of the perchloric acid extract are separated over an HPLC system using a glass "Microbore Column" having a diameter of 2.8 mm, which is packed to a height of 2 cm with TLC-4A-cation exchange resin (Durrum Chemical Corp., Palo Alto, Calif.). The column temperature is maintained at 65° C. by means of a water bath with circulating water. The column is eluted at a flow rate of 16 ml/h with an initial column pressure of 34.45 bar, which decreases as the ionic strength of the elution buffer increases. Buffer 1 (which contains 0.2M boric acid, 0.5M NaCl, 0.03% Brij 35 (polyoxyethylene monolauryl ether, the number of ethyleneoxy radicals is approximately 23; Pierce Chemical Co., Rockford, Ill.) and 0.0001% octanoic acid, pH adjusted to 6.0 with saturated KOH) is flushed through the column for 4 minutes. Buffer 2 (which contains 0.2M boric acid, 2.15M NaCl, 0.03% Brij 35 and 0.0001% octanoic acid, pH adjusted as above) is pumped through for 6 minutes. Buffer 3 (which contains 0.2M boric acid, 2.9M NaCl and 0.0001% octanoic acid (pH adjusted as above)) is likewise applied for 6 minutes. The column is re-equilibrated for 10 minutes with buffer 1, before the next sample is introduced. The column eluate is derivatised with 0.05% o-phthalaldehyde (Durrum Chemical Corp.) in 0.4M borate buffer (pH 10.4)/1 mM 2-mercaptoethanol/0.09% Brij 35. The flow rate for o-phthalaldehyde is 8 ml/h. The derivatised eluate is examined for its polyamine content by being passed through the flow cell of a flow-measuring device (Fluoro-Monitor; American Instrument Co., Silver Spring, Md.) with a fixed excitation wavelength of 360 nm and an emission wavelength of 570 nm. The data are determined using a Hewlett-Packard Model 3385A automation system. The variance of the system for a standard with known concentrations of putrescine, spermidine and sperminc hydrochloride is lower than 5%. The sensitivity of the HPLC system is approximately 50 pmol/50 gl sample ($10^6$ cells).

Using this method it is possible to observe a reduction in the polyamine levels with the compounds of formula I of the present invention. In particular, at a concentration of a compound of formula I of from 5 to 50 µM, for example 10 µM, the average levels of putrescine, spermidine and spermine are each reduced to less than 50% of the control values, especially to from 1 to 40% in the case of putrescine and spermidine and from 20 to 70% in the case of spermine.

As polyamine antimetabolites, the compounds of formula I have antiproliferative properties which can be demonstrated, for example, by means of the inhibitory action on the growth of human T24 bladder cell carcinomas. This is demonstrated by incubating the cells in "Eagles minimal essential medium" (see Eagle, H., Science 130, c 1432–1437 (1959)), to which 5% (v/v) foetal calf serum is added, in a humidified incubator at 37° C. and 5% by volume $CO_2$ in the air. The carcinoma cells (1000–1500) are transferred to 96-well microlitre plates and are incubated overnight under the said conditions. The test compound is added in serial dilutions on day 1. The plates are incubated under the said conditions for 5 days. During that period, control cultures undergo at least 4 cell divisions. After incubation, the cells are fixed with 3.3% (weight/volume=w/v) aqueous glutaraldehyde solution, washed with water and stained with 0.05% (w/v) aqueous methylene blue solution. After washing, the dye is eluted with 3% (w/v) aqueous hydrochloric acid. The optical density (OD) per well, which is directly proportional to the number of cells, is then measured by means of a photometer (Titertek multiskan) at 665 nm.

The $IC_{50}$ values are calculated by means of a computer system using the formula $$\frac{OD_{665}(\text{test}) - OD_{665}(\text{start})}{OD_{665}(\text{control}) - OD_{665}(\text{start})} \times 100$$

The $IC_{50}$ value is defined as the concentration of active ingredient at which the number of cells per well at the end of the incubation period is only 50% of the number of cells in the control cultures.

For compounds of formula I, $IC_{50}$ values in the range of from $2 \times 10^{-4}$ to $5 \times 10^{-8}$ M, especially in the range of from $3 \times 10^{-5}$ to $10^{-7}$ M, are obtained.

The compounds of formula I are therefore especially suitable for the (therapeutic or preventive) treatment of pathological conditions that are responsive to a reduction in the concentration of polyamines in cells (intracellular polyamine concentration), for example proliferative disorders, especially benign and malignant tumour disorders. They can bring about the regression of tumours and also prevent the spread of tumour cells (metastasisation) and the growth of micrometastases. Moreover, they can be used, for example, for treating protozoal infections, such as, for example, trypanosomiasis, malaria, or pulmonary inflammation caused by Pneumocystis carinii.

The compounds of formula I can be used as polyamine antimetabolites either on their own or in combination with other pharmacologically active substances. They may be combined with, for example, (a) inhibitors of one or more enzymes of polyamine biosynthesis, for example ornithine decarboxylase or S-adenosylmethionine decarboxylase inhibitors, (b) inhibitors of protein kinase C, (c) inhibitors of tyrosine protein kinase, (d) cytokines, (e) negative growth regulators, (f) aromatase inhibitors, (g) antioestrogens or (h) conventional cytostatic active ingredients.

Preference is given to compounds of formula I wherein $R_1$ and $R_2$, each independently of the other, am selected from $C_2$–$C_7$alkyl, especially $C_2$–$C_4$alkyl, such as ethyl, n-propyl, isopropyl, isobutyl or n-butyl; $C_3$–$C_7$alkenyl wherein the double bond does not originate from the carbon atom that is bonded to a nitrogen bonding $R_1$ or $R_2$, especially $C_3$–$C_4$-alkenyl, such as allyl; $C_3$–$C_7$alkynyl wherein the triple bond does not originate from the carbon atom that is bonded to a nitrogen bonding $R_1$ or $R_2$, especially $C_3$–$C_4$alkynyl, such as propargyl; and $C_3$–$C_5$cycloalkyl-$C_1$–$C_2$alkyl, especially $C_3$–$C_4$cycloalkylmethyl, such as cyclopropylmethyl; as well as from $C_3$–$C_5$cycloalkyl, such as cyclopropyl or cyclobutyl; or salts thereof.

Greater preference is given to compounds of formula I wherein $R_1$ and $R_2$, each independently of the other, are selected from $C_2$–$C_4$alkyl, such as ethyl, n-propyl, n-butyl or isobutyl, and $C_3$–$C_4$alkenyl wherein the double bond does not originate from the carbon atom that is bonded to a nitrogen bonding $R_1$ or $R_2$, such as allyl or crotonyl, and also from $C_3$–$C_4$alkynyl wherein the triple bond does not originate from the carbon atom that is bonded to a nitrogen bonding $R_1$ or $R_2$, such as propargyl, and (also) from $C_3$–$C_4$cycloalkylmethyl, such as cyclopropylmethyl, especially with the proviso that $R_1$ and $R_2$ together have not more than 6 carbon atoms, or salts thereof.

Special preference is given to compounds of formula I wherein $R_1$ and $R_2$, each independently of the other, are selected from ethyl, n-propyl, isopropyl, n-butyl, isobutyl and allyl, or salts thereof, especially those compounds wherein $R_1$ and $R_2$ together have 4, 5 or 6 carbon atoms, or salts thereof.

Very special preference is given to compounds of formula I wherein $R_1$ is ethyl and $R_2$ is selected from ethyl, n-propyl, n-butyl, isobutyl and allyl, or salts thereof.

Most especially preferred are the individual compounds of formula I mentioned in the Examples, especially those wherein $R_1$ and $R_2$ together have from 4 to 6 carbon atoms, most especially those wherein neither $R_1$ nor $R_2$ is lower alkynyl and wherein $R_1$ and $R_2$ are each bonded via methylene (—$CH_2$—), or salts thereof.

The compounds according to the invention are prepared for example by a) nucleophilically substituting an amino compound of formula II

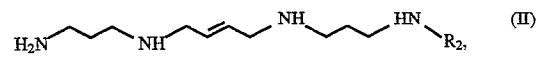

wherein $R_2$ is as defined for compounds of formula I and any functional groups that are not to take pan in the reaction are, if necessary, in protected form, with a compound of formula III $$R_1\text{—}X \qquad (III),$$

wherein $R_1$ is as defined for compounds of formula I and X is a nucleofugal leaving group, with only one of the radicals $R_1$ and $R_2$ being methyl, and removing any protecting groups that are present, or b) for the preparation of compounds of formula I wherein $R_1$ and $R_2$ are the same and each have one of the meanings given in the definition of those radicals in compounds of formula I, other than methyl, nucleophilically substituting a diamine of formula IV

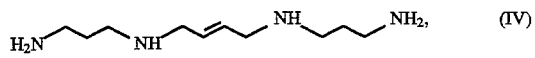

wherein any functional groups that are not to take part in the reaction are, if necessary, in protected form, with a compound of formula V $$R^x\text{—}X \qquad (V),$$

wherein $R^x$ has one of the meanings given for $R_1$ or $R_2$ in compounds of formula I, other than methyl, and X is a nucleofugal leaving group, and removing any protecting groups that are present, or c) for the preparation of compounds of formula I wherein $R_1$ and $R_2$ are each independently of the other a radical $R_1$ or $R_2$ that is bonded via a methylene group (—$CH_2$—) belonging to the radical in question, reacting a diamide of formula VI

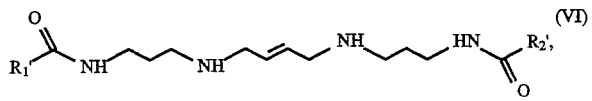

wherein $R_1'$ and $R_2'$ are each independently of the other the radicals, minus the above-mentioned methylene group, which are complementary to the last-defined radicals $R_1$ and $R_2$, and any functional groups that are not to take part in the reaction are, if necessary, in protected form, with selective reduction of the two amide groups, and, if necessary, removing any protecting groups that are present, or d) reacting a hexahydropyrimidine derivative of formula VII

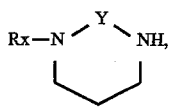

(VII)

wherein Rx is one of the radicals indicated for $R_1$ and $R_2$ under formula I and Y is a divalent protecting group, with an olefin of formula VIII

(VIII)

wherein Q and Q' are each independently of the other a nucleofugal leaving group, with nucleophilic substitution of the two nucleofugal leaving groups, and removing any protecting groups that are present, and, if desired, converting an obtainable free compound of formula I into its salt, convening an obtainable salt of a compound of formula I into the free compound or into a different salt of a compound of formula I, and/or separating obtainable mixtures of isomers into the individual isomers.

In the following more detailed description of the preferred processes, $R_1$ and $R_2$ are as defined for compounds of formula I, unless indicated otherwise.

Process a) (alkylation): In the starting materials of formula II, all the nitrogen atoms are preferably in mono-protected form, so that the hydrogen that is to be replaced by $R_1$ is still present; in that case the 4 nitrogen atoms are each bonded to a protecting group instead of to one of the 4 hydrogen atoms shown in formula II that are not to be reacted.

The protecting groups are protecting groups that can be removed without reduction of the central double bond in the molecule of formula II taking place.

The protecting groups for functional groups in starting materials the reaction of which is to be avoided, that is to say amino and imino groups and hydroxy groups, include especially those protecting groups (conventional protecting groups) that are conventionally employed in the synthesis of peptide compounds and also of cephalosporins and penicillins as well as nucleic acid derivatives. Those protecting groups may already be present in the precursors and are intended to protect the functional groups in question from undesired secondary reactions, such as acylations, esterifications, oxidations, solvolyses, etc. A characteristic of protecting groups is that they are readily removable, that is to say without undesired secondary reactions taking place, for example by solvolysis, by reduction (without the simultaneous reduction of double bonds or of triple bonds that may be present), by photolysis or enzymatically, for example also under physiological conditions. A characteristic of protecting groups is that they are not present in the end products.

The protection of functional groups by such protecting groups, the protecting groups themselves and the reactions for their removal are described, for example, in standard works, such as J. F. W. McOmie, "Protective Groups in Organic Chemistry", Plenum Press, London and New York 1973, in Th. W. Greene, "Protective Groups in Organic Synthesis", Wiley, New York 1981, in "The Peptides"; Vol. 3 (E. Gross and J. Meienhofer, eds.), Academic Press, London and New York 1981, in "Methoden der organischen Chemie", Houben-Weyl, 4th edition, Vol. 15/I, Georg Thieme Verlag, Stuttgart 1974, and in H.-D. Jakubke and H. Jescheit, "Aminosäuren, Peptide, Proteine", Verlag Chemie, Weinheim, Deerfield Beach and Basle 1982.

A protected amino or imino group is protected by a monovalent amino-protecting group, for example in the form of an acylamino, arylmethylamino, 2-acyl-lower alk-1-enylamino or silylamino group. Divalent protecting groups bridging two adjacent nitrogen atoms are also possible.

Hereinafter an "amino"-protecting group is always to be understood as meaning also a corresponding imino-protecting group.

In an acylamino group acyl is, for example, the acyl radical of an organic carboxylic acid having, for example, up to 18 carbon atoms, especially of a lower alkanecarboxylic acid that is unsubstituted or substituted by, for example, halogen or aryl, or of a benzoic acid that is unsubstituted or substituted by, for example, halogen, lower alkoxy or nitro, or preferably of a carbonic acid semiester. Such acyl groups are preferably lower alkanoyl, such as formyl, acetyl, propionyl or pivaloyl, halo-lower alkanoyl, for example 2-haloacetyl, such as 2-chloro-, 2-bromo-, 2-iodo-, 2,2,2-trifluoro- or 2,2,2-trichloro-acetyl, benzoyl that is unsubstituted or substituted by, for example, halogen, lower alkoxy or nitro, such as benzoyl, 4-chlorobenzoyl, 4-methoxybenzoyl or 4-nitrobenzoyl, lower alkoxycarbonyl, lower alkoxycarbonyl that is branched preferably at the 1-position of the lower alkyl radical or that is suitably substituted at the 1- or 2-position, for example tert-lower alkoxycarbonyl, such as tert-butoxycarbonyl, arylmethoxycarbonyl having one, two or three aryl radicals which are phenyl that is unsubstituted or mono- or polyo-substituted, for example, by lower alkyl, especially tert-lower alkyl, such as tert-butyl, lower alkoxy, such as methoxy, hydroxy, halogen, such as chlorine, and/or by nitro, for example benzyloxycarbonyl, 4-nitrobenzyloxycarbonyl, diphenylmethoxycarbonyl, 9-fluorenylmethoxycarbonyl or di(4-methoxyphenyl)methoxycarbonyl, aroylmethoxycarbonyl wherein the aroyl group is preferably benzoyl that is unsubstituted or substituted by, for example, halogen, such as bromine, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, 2-(trisubstituted silyl)-lower alkoxycarbonyl, for example 2-tri-lower alkylsilyl-lower alkoxycarbonyl, such as 2-trimethylsilylethoxycarbonyl or 2-(di-n-butylmethylsilyl)ethoxycarbonyl, or triarylsilyl-lower alkoxycarbonyl, for example 2-triphenylsilylethoxycarbonyl. Especially important amino- (and imino-)acyl-protecting groups are suitable organic sulfonic acid radicals, such as arylsulfonic acid radicals, especially phenyl- or lower alkylphenyl-sulfonyl radicals, such as benzene- or toluene-sulfonyl, or aryl-lower alkylsulfonyl radicals, especially phenyl- or lower alkylphenyl-sulfonyl, such as benzyl- or 4-methylbenzyl-sulfonyl; and/or suitable organic phosphoryl radicals, such as diarylphosphinyl, especially diphenylphosphinyl ($[Phe]_2$ (P=O)—), or, most especially, di(lower alkoxy)phosphoryl, such as diethoxyphosphoryl ($[H_3C—CH_2O—]_2—(P=O)—$).

In an arylmethylamino group, for example a mono-, di- or, especially, tri-arylmethylamino group, the aryl radicals are especially unsubstituted or substituted phenyl radicals. Such groups are, for example, benzyl-, diphenylmethyl- or, especially, trityl-amino.

In a 2-acyl-lower alk-1-enyl radical that may be used as an amino-protecting group, acyl is, for example, the corresponding radical of a lower alkanecarboxylic acid, of a benzoic acid that is unsubstituted or substituted, for example, by lower alkyl, such as methyl or tert-butyl, lower alkoxy, such as methoxy, halogen, such as chlorine, and/or by nitro, or especially of a carbonic acid semiester, such as a carbonic acid lower alkyl semiester. Corresponding protecting groups are especially 1-lower alkanoyl-lower alk-1-en-2-yl, for example 1-lower alkanoyl-prop-1-en-2-yl, such as 1-acetyl-prop-1-en-2-yl, or lower alkoxycarbonyl-lower alk-1-en-2-yl, for example lower alkoxycarbonyl-prop-1-en-2-yl, such as 1-ethoxycarbonyl-prop-1-en-2-yl.

A silylamino group is, for example, a tri-lower alkylsilylamino group, for example trimethylsilylamino or tert-butyldimethylsilylamino. It is also possible for the silicon atom of the silylamino group to be substituted by only two lower alkyl groups, for example methyl groups, and by the amino group or carboxy group of a second molecule of formula I. Compounds having such protecting groups may be prepared, for example, using the corresponding chlorosilanes, such as dimethylchlorosilane, as silylating agent.

Preferred amino-protecting groups are lower alkoxycarbonyl, phenyl-lower alkoxycarbonyl, fluorenyl-lower alkoxycarbonyl, 4-lower alkylphenylsulfonyl, di(lower alkoxy)phosphoryl, 2-lower alkanoyl-lower alk-1-en-2-yl or lower alkoxycarbonyl-lower alk-1-en-2-yl, with tert-butoxycarbonyl, toluenesulfonyl and/or diethoxyphosphoryl being especially preferred.

Preferred are also two divalent amino-protecting groups (preferably bridging adjacent nitrogen atoms, such as $N^1$ and $N^5$ or $N^{10}$ and $N^{14}$), such as unsubstituted or mono- or di-substituted methylene groups, such as 1-lower alkoxy (for example methoxy or ethoxy)lower alkylene (for example ethylene or 1-n-butylene), for example $—C(CH_3)(OC_2H_5)—$, especially mono- or di-lower alkyl- or phenyl-methylene, for example $—C(CH_3)_2—$ or $—CH(-phenyl)—$; methylene ($—CH_2—$) is especially preferred.

In the starting materials of formula III, X is preferably a nucleofugal group, preferably arylsulfonyloxy, such as toluenesulfonyloxy, lower alkanesulfonyloxy, such as methanesulfonyloxy, or especially halogen, such as chlorine, bromine or iodine, most especially bromine or iodine.

The reaction is preferably carried out in the presence of a strong base, such as an alkali metal hydride, for example sodium hydride or potassium hydride, or also an alkali metal amide, such as sodium amide, or an alkali metal di-lower alkylamide, such as lithium diisopropylamide, especially in the presence of sodium hydride or potassium hydride, which may be added, for example, in the form of a dispersion in oil or after extraction of the oil, for example with a liquid hydrocarbon, such as hexane, using the base in an equimolar amount or preferably in excess relative to the molar amount of the compound of formula II, for example in an amount of from 1 to 20 times the molar amount, especially from 2 to 10 times the molar amount, at preferred temperatures of from −10° C. to the reflux temperature of the reaction mixture, especially from approximately 5 to approximately 40° C., for example at room temperature, or (when starting materials containing phosphoryl-protected amino groups are used) at from 10° C. to the reflux temperature, for example at from 20° to 80° C., in aprotic, especially polar, solvents, such as acid amides, for example dimethylformamide, diethylformamide, 1,3-dimethyl-3,4,5,6-tetrahydro-2(1H)-pyrimidinone (DMPU) or hexamethylphosphoric acid triamide, aromatic hydrocarbons, such as toluene or benzene (in which case preferably in the presence of a phase transfer catalyst, for example a tetra-lower alkylammonium halide, such as tetra(n-butyl)ammonium bromide), or mixtures of such solvents, in the presence or absence of a protecting gas, such as argon or nitrogen; ammonia that is formed when alkali metal amides are used as bases is preferably removed by the application of a vacuum, for example of from 0.1 to 100, especially from 0.5 to 10, torr.

It is preferred to use the compound of formula III also in an equimolar amount or in excess relative to the compound of formula II, especially in an amount that is from 1 to 20 times the molar amount, especially from 2 to 10 times the molar amount, relative to the compound of formula II.

When the protecting group at the nitrogen atom to be alkylated by $R_1$ is an organic sulfonic acid radical, such as arylsulfonyl, especially phenylsulfonyl or lower alkylphenylsulfonyl, such as benzene- or toluene-sulfonyl, or aryl-lower alkylsulfonyl, especially phenyl- or lower alkylphenylsulfonyl, such as benzyl- or 4-methylbenzyl-sulfonyl, the alkylation with a compound of formula III can preferably be carried out in the presence of relatively weak bases, such as especially metal hydroxides or carbonates, such as especially alkali metal hydroxides, for example sodium or potassium hydroxide, or in the presence of alkaline earth metal carbonates or alkali metal carbonates, for example sodium or potassium carbonate, preferably in the last-mentioned solvents, especially in halogenated hydrocarbons, such as dichloromethane or chloroform, and most especially in carboxylic acid amides, such as dimethylformamide or dimethylacetamide, and at the temperatures indicated and preferably under a protecting gas, such as nitrogen or argon.

The following applies in respect of the subsequent removal of the protecting groups:

A protected amino or imino group is freed in a manner known per se and, depending on the nature of the protecting groups, by different methods, preferably by means of solvolysis or selective reduction, for example as described in the standard works mentioned at the beginning. Lower alkoxycarbonylamino, such as tert-butoxycarbonylamino, arylmethoxycarbonylamino, such as (unsubstituted or substituted) benzyloxycarbonylamino, or di(lower alkoxy) phosphoryl can be removed in the presence of acids, for example mineral acids, e.g. a hydrogen halide, such as hydrogen chloride or hydrogen bromide, or of sulfuric or phosphoric acid, preferably in the presence of hydrogen chloride, in polar solvents, such as water, alcohols, such as lower alkanols, e.g. methanol or ethanol, a carboxylic acid, such as acetic acid, or ethers, preferably cyclic ethers, such as tetrahydrofuran or dioxane (preferred in the case of di-lower alkoxyphosphoryl removal), or mixtures of two or more of the mentioned solvents, especially in aqueousalcoholic solutions, such as water/methanol mixtures; and 2-halo-lower alkoxycarbonylamino (optionally after conversion of a 2-bromo-lower alkoxycarbonylamino group into a 2-iodo-lower alkoxycarbonylamino group), aroylmethoxycarbonylamino or 4-nitrobenzyloxycarbonylamino can be removed, for example, by treatment with a suitable reducing agent, such as zinc in the presence of a suitable carboxylic acid, such as aqueous acetic acid. Aroylmethoxycarbonylamino can be removed also by treatment with a nucleophilic, preferably salt-forming reagent, such as sodium thiophenolate, and 4-nitrobenzyloxycarbonylamino can be removed also by treatment with an alkali metal dithionite, for example sodium dithionite. Unsubstituted or substituted diphenylmethoxycarbonylamino, tert-lower alkoxycarbonylamino or 2-(trisubstituted silyl)-lower alkoxycarbonylamino, such as 2-tri-lower alkylsilyl-lower alkoxycarbonylamino, can be removed by treatment with a suitable acid, for example formic acid or trifluoroacetic acid, and unsubstituted or substituted triarylmethylamino or formylamino can be removed, for example, by treatment with an acid, such as a mineral acid, for example hydrochloric acid, or an organic acid, for example formic acid, acetic acid or trifluoroacetic acid, in the absence or presence of water, and an amino group protected in the form of silylamino can be freed, for example, by means of hydrolysis or alcoholysis. An amino group protected by 2-haloacetyl, for example 2-chloroacetyl, can be freed by treatment with thiourea in the presence of a base, or with a thiolate salt, such as an alkali metal thiolate, of thiourea, and subsequent solvolysis, such as alcoholysis or hydrolysis, of the resulting substitution product. An amino group protected by 2-(trisubstituted silyl)-lower alkoxycarbonyl, such as 2-tri-lower alkylsilyl-lower alkoxycarbonyl, can be converted into free amino (or imino) also by treatment with a salt of hydrofluoric acid that yields fluoride anions, such as an alkali metal fluoride, for example sodium or potassium fluoride, in the absence or presence of a macrocyclic polyether ("crown ether"), or with a fluoride of an organic quaternary base, such as tetra-lower alkylammonium fluoride or tri-lower alkylaryl-lower alkylammonium fluoride, for example tetraethylammonium fluoride or tetrabutylammonium fluoride, in the presence of an aprotic, polar solvent, such as dimethyl sulfoxide or N,N-dimethylacetaminde. Likewise, silyl, such as trimethylsilyl, bonded directly to a hetero atom, such as nitrogen, can be removed by means of fluoride ions. An amino group protected by diarylphosphinyl, such as diphenylphosphinyl, can be freed in the presence of a Lewis acid, especially boron trifluoride etherate, such as boron trifluoride ethyl etherate or methyl etherate, in suitable solvents or solvent mixtures, for example alcohols, such as methanol or ethanol, halogenated hydrocarbons, such as chloroform or methylene chloride, ethers, such as dimethyl or diethyl ether, or especially mixtures thereof, such as methanol/methylene chloride/dimethyl or diethyl ether, at preferred temperatures of from −10° C. to the respective reflux temperature, especially from 0° C. to room temperature, preferably under a protecting gas, such as $N_2$.

An amino group protected in the form of a sulfonamide is preferably freed by acid hydrolysis, for example in the presence of a mineral acid, such as especially a hydrohalic acid, such as hydrobromic acid, in an alcohol, especially an aryl alcohol, such as phenol, in the presence or absence of a carboxylic acid, such as a lower alkanoic acid, for example acetic acid, at preferred temperatures of from 60° C. to the reflux temperature, or by acid hydrolysis with concentrated sulfuric acid.

An amino group protected by di(lower alkoxy)phosphoryl is preferably freed by acid hydrolysis, for example in the presence of a hydrogen halide, such as hydrogen bromide or especially hydrogen chloride (which is preferably introduced in gaseous form), in an ether, especially a cyclic ether, such as tetrahydrofuran, at preferred temperatures of from −10° C. to the reflux temperature of the reaction mixture in question, for example at from approximately 0° C. to approximately room temperature.

Nitrogen atoms protected by a divalent protecting group bridging two adjacent nitrogen atoms are preferably freed by acidolytic cleavage, for example with mineral acids, such as hydrohalic acids, for example hydrochloric or hydrobromic acid, or under milder conditions similar to Knoevenagel conditions, for example with malonic acid or cyanoacetic acid in the presence of a tertiary nitrogen base, such as pyridine (see, for example, Nagarajan et at., J. Org. Chem. 50, 5735–5737 (1985)).

The temperatures at which the protected functional groups are freed are preferably from −80° C. to reflux temperature, especially preferably from −20° to 50° C. or from 80° to 110° C., for example from 0° to 35° C., such as in the range of from 0° C. to room temperature, or approximately at reflux temperature.

When several protected functional groups are present, the protecting groups may, if desired, be so selected that it is possible to remove more than one such group simultaneously. Conversely, the groups may also be so selected that they are not all removed simultaneously but can be removed in a desired sequence, in which case the corresponding intermediates are obtained.

The introduction of amino- and/or imino-protecting groups that is necessary for the preparation of protected starting materials of formula II is effected in a manner known per se, for example as described in the above-mentioned standard works, and may be carried out stepwise or, preferably, in a single procedure.

For the introduction of the acyl protecting group of a carbonic acid semiester, such as lower alkoxycarbonyl, there are suitable especially symmetrical or mixed carbonic acid anhydrides, such as di-lower alkyl dicarbonate, for example di-tert-butyl dicarbonate, or lower alkoxycarboxylic acid azides, such as tert-butoxycarboxylic acid azide, or other activated carbonic acid semiester derivatives, such as imidazolides, for example lower alkoxy-, such as tert-butoxy-carboxylic acid 1-imidazolide, or especially 2-(tert-butoxycarbonyl-oxyimino)-2-phenylacetonitrile.

For the introduction of organic sulfonic acid radicals, such as arylsulfonic acid radicals, especially phenyl- or lower alkylphenyl-sulfonyl radicals, such as benzene- or toluenesulfonyl, or aryl-lower alkylsulfonyl radicals, especially phenyl- or lower alkylphenylsulfonyl, such as benzyl- or 4-methylbenzyl-sulfonyl, there are suitable especially corresponding sulfonyl halides, such as sulfonyl chlorides or bromides, for example toluenesulfonic acid chloride.

For the introduction of suitable organic phosphoryl radicals, such as diarylphosphinyl, especially diphenylphosphinyl, or more especially di(lower alkoxy) phosphoryl, such as diethoxyphosphoryl, there is suitable especially reaction with corresponding phosphoryl halides, for example chlorides, such as diphenylphosphinyl chloride (see Osborn, H. M. I., et al., Synlett 2, 145–147 (1994)), or iodides, such as di-lower alkoxyphosphoryl iodide (which can be prepared, for example, electrochemically in situ in acetonitrile on platinum electrodes in supporting electrolytes, such as tetra-lower alkylammonium halides, for example tetraethylammonium bromide, see J. Gen. Chem. (USSR) 62, 370 (1992)); or (for the introduction especially of di(lower alkoxy)phosphoryl) from the corresponding phosphites, such as all(lower alkyl) phosphite, especially diethyl phosphite, under substantially anhydrous conditions, for example by phase transfer catalysis in the presence of a phase transfer catalyst, for example of a tetra-lower alkylammonium halide, such as tetra(n-butyl)ammonium bromide; in the presence (in each case preferably in excess, for example in a 2- to 20-fold molar excess, relative to the base to be protected) of a dehydrating inorganic salt, such as potassium carbonate, and of a base that can be convened by the phase transfer catalyst from the solid form into the organic solution, such as potassium hydrogen carbonate; in suitable organic solvents or solvent mixtures, such as halogenated hydrocarbons, for example methylene chloride or carbon tetrachloride, or mixtures thereof; at preferred temperatures of from 0° to 40° C., for example at from approximately 10° to approximately 30° C. (see J. Org. Chem. 56, 4904–4907 (1991)); reaction without a phase transfer catalyst also being possible.

For the introduction of divalent amino-protecting groups, such as unsubstituted or monoor di-substituted methylene groups, such as 1-lower alkoxy (for example methoxy or ethoxy)-lower alkylene (for example ethylene or 1-n-butylene), for example —$C(CH_3)(OC_2H_5)$—, conventional methods are used. Especially for the introduction of monoor di-lower alkyl- or phenyl-methylene, for example —C(CH$_3$)$_2$— or —CH(-phenyl)—, especially —CH$_2$—, there are suitable corresponding aldehydes or ketones in which there is an oxo group in place of the two bonds indicated in the formulae shown above, for example benzaldehyde or especially acetone or most especially formaldehyde.

The introduction is carded out under customary conditions, preferably in solvents, such as carboxylic acid amides, for example dimethyl- or diethyl-formamide, in chlorinated hydrocarbons, such as carbon tetrachloride, chloroform or methylene chloride, or in ethers, such as cyclic ethers, for example tetrahydrofuran, or mixtures thereof, in the case of the introduction of sulfonyl radicals additionally in the presence of water (biphasic system) and in the case of the introduction of unsubstituted, mono- or di-substituted methylene groups also if desired additionally or exclusively in the presence of water, it being possible in each case for the water to contain a base, such as an alkali metal hydroxide, such as sodium or potassium hydroxide, if necessary under a protecting gas, such as nitrogen or argon, and if necessary in the presence of bases, such as tertiary nitrogen bases, for example triethylamine, pyridine or 4-dimethylaminopyridine, or of morpholine, or hydroxides, such as ammonium hydroxide or alkali metal hydroxides, for example sodium or potassium hydroxide.

Preferred temperatures are from −10° to 50° C., especially from 0° to 30° C.

Where indicated, the conditions mentioned specifically in each particular case are preferred.

Starting materials of formula II can preferably be prepared from a compound of formula IV by, especially, reacting a compound of formula IV that is protected analogously to a compound of formula II (as described above) and wherein all four nitrogen atoms are protected but a hydrogen is bonded to the nitrogen to be reacted at least at the position at which R$_2$ is to be introduced, with a compound of formula IX

R$_2$—X                                                                 (IX), wherein R$_2$ is as defined for compounds of formula I and X is as defined under formula III, under conditions analogous to those described for process a), and obtaining the corresponding compound of formula II by, if necessary, removing some of the protecting groups at the terminal nitrogen to which R$_1$ is to be bonded, or by removing all the protecting groups and then re-introducing protecting groups, as described for compounds of formula II. A compound of formula II protected as described above may also be isolated as a secondary product of process b).

Process variant a) is suitable especially for the introduction of radicals R$_1$ and R$_2$ that are different from each other, in which case corresponding non-symmetrical compounds of formula I are obtained, or for the introduction of sterically hindered radicals, such as isobutyl or isopropyl.

Process b) (alkylation): In the starting materials of formula IV, all the nitrogen atoms are preferably in mono-protected form, so that the hydrogen that is to be replaced by R$_1$ and R$_2$ is still present; in that case the 4 nitrogen atoms are each bonded to a protecting group instead of to one of the 4 hydrogen atoms shown in formula IV that are not to be reacted.

In compounds of formula V, X is as defined above for compounds of formula III.

The protecting groups, the process conditions for the reaction, including the molar ratios of the starting materials, the removal of protecting groups and the introduction of protecting groups are preferably analogous to those described under process a), where compounds of formula IV are used instead of compounds of formula II and compounds of formula V are used instead of compounds of formula III.

The reaction is suitable especially for the introduction of two radicals R$_1$ and R$_2$ that are the same. In that case, symmetrically substituted compounds of formula I are formed.

Compounds of formula II can be obtained as secondary product in this reaction, in some cases in a relatively large amount, and can be isolated and used in process a). This is a preferred method of synthesis for the preparation of non-symmetrical compounds of formula I.

The unprotected starting material of formula IV is known, is obtainable e.g. by reaction of trans-1,4-dichloro-2-butene with 3-aminopropylamine protected at an amino nitrogen and subsequent removal of the protecting groups or is available commercially (e.g. from Carbolabs, Inc., New Haven, Conn., USA; or Ames Laboratories, Inc., Milford, Conn., USA).

Process c) (reduction of amides): In the diamides of formula VI wherein R$_1$' and R$_2$' are each independently of the other the radicals, minus the above-mentioned methylene group, which are complementary to the last-defined radicals R$_1$ and R$_2$, and any functional groups that are not to take part in the reaction are, if necessary, in protected form, R$_1$'—(C=O)— and R$_2$'—(C=O)— are each independently of the other especially unsubstituted C$_1$–C$_6$alkyl-(C=O)— (yields a C$_1$–C$_7$alkyl radical R$_1$ or R$_2$ bonded via methylene), which may, however, also be substituted by fluorine, especially by up to three fluorine atoms; C$_2$–C$_6$alkenyl-(C=O)— (yields a C$_3$–C$_7$alkenyl radical R$_1$ or R$_2$ bonded via methylene), preferably C$_2$–C$_3$alkenyl-(C=O)—, e.g. vinyl-(C=O)— or allyl-(C=O)—; C$_2$–C$_6$alkynyl-(C=O)— (yields a C$_3$–C$_7$alkynyl radical R$_1$ or R$_2$ bonded via methylene), especially C$_2$–C$_3$-alkynyl-(C=O)—, e.g. ethynyl or propyn-1-yl; or cycloalkyl-C$_1$–C$_6$alkyl-(C=O)— (yields a cycloalkyl-C$_2$–C$_7$alkyl radical R$_1$ or R$_2$ bonded via a methylene group) or cycloalkyl-(C=O)—, wherein cycloalkyl is especially a radical having from 3 to 5 carbon atoms, especially cyclopropyl or also cyclobutyl, and the C$_1$–C$_6$alkyl radical (if present) is preferably a radical defined as above, especially C$_1$–C$_2$alkyl, for example methyl or ethyl, especially methyl, e.g. cyclopropyl-methyl-(C=O)—, cyclobutyl-(C=O)— or most especially cyclopropyl-(C=O)—.

The two radicals R$_1$' and R$_2$' may be different or, especially, the same. The resulting radicals R$_1$ and R$_2$ are without primary branching at the bonding carbon atom.

The selective reduction of the two amide groups may be carded out simultaneously or stepwise. "Selective" means that the reducing agent does not at the same time reduce the central double bond and any further olefinic bonds or carbon-carbon triple bonds that are present, but protecting groups removable under the corresponding conditions can be removed virtually at the same time (i.e. in the same procedure) as the amide group reduction. Suitable selective reducing agents are especially certain complex hydrides, such as NaAl(OCH$_2$CH$_2$OCH$_3$)$_2$H$_2$ (=sodium dihydro-bis (2-methoxyethoxy)aluminate ), which can be added in the form of a solution in an aromatic hydrocarbon, such as toluene, or lithium aluminium hydride, which are preferably used in ethers as solvents, such as cyclic ethers, for example dioxane or tetrahydrofuran, or in di-lower alkyl ethers, such as diethyl ether, with heating, for example at reflux temperature (especially in the case of diethyl ether or tetrahydrofuran) or at temperatures below the reflux temperature, for example at from 20° to 35° C.

Since secondary reactions may occur in this process, processes a), b) or d) are preferred.

The protecting groups and their introduction and removal are preferably as described under process a). Preferred protecting groups are the mentioned divalent protecting groups selected from unsubstituted, mono- or di-substituted methylene, especially methylene, as a bridge between $N^1$ and $N^5$ as well as between $N^{10}$ and $N^{14}$, which are introduced as described above.

The starting materials of formula VI can be prepared in particular, compounds of formula VI'

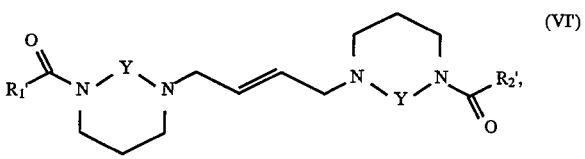
(VI')

wherein $R_1'$ and $R_2'$ are as defined and Y is one of the above-mentioned divalent amino-protecting groups, especially methylene, (these are preferred compounds of formula VI), can be prepared from corresponding precursors wherein there is a hydrogen atom in place of one or both of the radicals $R_1$—(C=O)— and $R_2$—(C=O)— and the remaining radicals are as last defined, by reacting those precursors with a carboxylic acid of formula X

and (especially when $R_1'$ and $R_2'$ in compounds of formula VI are different) then with a carboxylic acid of formula XI

wherein $R_1'$ and $R_2'$ are each as defined for compounds of formula VI, or preferably with reactive derivatives of the compounds of formula X and, where appropriate, of formula XI, under customary conditions for the preparation of acid amides.

Reactive acid derivatives are especially the corresponding symmetrical acid anhydrides of the formulae $R_1'$—(C=O)—O—(C=O)—$R_1'$ and $R_2'$—(C=O)—O—(C=O)—$R_2'$, or also asymmetrical acid anhydrides, especially the corresponding acid chlorides, acid azides or mixed anhydrides with acetic acid, or also the hydroxysuccinimide derivatives, all of which are known, can be prepared according to known processes or are available commercially.

Derivatives of carboxylic acids of formula X or XI, which are used as acylating agents, can also be formed in situ. For example, N,N'-disubstituted amidino esters can be formed in situ by reacting the mixture of the starting material of formula IV and the acid used as acylating agent in the presence of a suitable N,N'-disubstituted carbodiimide, for example N,N'-cyclohexylcarbodiimide. Furthermore, amino or amido esters of the acids used as acylating agent can be formed in the presence of the starting material of formula IV that is to be acylated, by reacting the mixture of the corresponding acid and amino starting materials in the presence of an N,N'-disubstituted carbodiimide, for example N,N'-dicyclohexylcarbodiimide, and of an N-hydroxy-imide, for example N-hydroxysuccinimide, in the absence or presence of a suitable base, for example 4-dimethylamino-pyridine. Moreover, activation can be carried out in situ by reaction with N,N,N',N'-tetraalkyluronium compounds, such as O-benzotriazol-1-yl-N,N,N',N'-tetramethyluronium hexafluorophosphate, O-(1,2-dihydro-2-oxo- 1-pyridyl)-N, N,N',N'-tetramethyluronium tetrafluoroborate or O-(3,4-dihydro-4-oxo- 1,2,3-benzo-triazolin-3-yl)-N,N,N',N'-tetramethyluronium tetrafluoroborate. Finally, phosphoric acid anhydrides of the carboxylic acids of formulae X or XI can be prepared in situ by reacting an alkylphosphoric acid amide, such as hexamethylphosphoric acid triamide, in the presence of a sulfonic acid anhydride, such as 4-toluenesulfonic acid anhydride, with a salt, such as a tetrafluoroborate, for example sodium tetrafluoroborate, or with another derivative of hexamethylphosphoric acid triamide, such as benzotriazol-1-yl-oxy-tris(dimethylamino) phosphonium hexafluoride, preferably in the presence of an additive, such as N-hydroxybenzotriazole.

The acylation is preferably carried out in an inert, aprotic, preferably anhydrous solvent or solvent mixture, for example in a carboxylic acid amide, for example formamide or dimethylformamide, a halogenated hydrocarbon, for example methylene chloride, carbon tetrachloride or chlorobenzene, a ketone, for example acetone, a cyclic ether, for example tetrahydrofuran, an ester, for example ethyl acetate, or a nitrile, for example acetonitrile, or in a mixture thereof, where appropriate at reduced or elevated temperature, for example in a temperature range of from approximately −40° C. to approximately +100° C., preferably from approximately −10° C. to approximately +50° C., in the case where arylsulfonyl esters are used at approximately from +100° C. to +200° C., and where appropriate under an inert gas atmosphere, for example under a nitrogen or argon atmosphere.

Aqueous, for example alcoholic, solvents, e.g. ethanol, or aromatic solvents, e.g. benzene or toluene, are also possible.

The reaction is preferably carried out in the presence of tertiary nitrogen bases, such as pyridine or triethylamine, also 4-dimethylaminopyridine or N-methyl-morpholine. The mentioned bases, especially pyridine, may be present instead of a solvent; that is preferably the case when symmetrical anhydrides are used as reactive acid derivatives (those anhydrides are then used preferably in a molar excess relative to the amine to be acylated, preferably in a 1.2- to 10-fold excess).

The precursors of the compounds of formula VI', wherein a hydrogen atom is present in place of one or both of the radicals $R_1$—(C=O)— and $R_2$—(C=O)— and the remaining radicals are as defined, are prepared, for example, by introducing the divalent amino-protecting groups Y into a compound of formula IV under conditions such as those described in the more detailed description of process variant a), preferably using formaldehyde in order to introduce two methylene protecting groups, as described therein.

Process d) (nucleophilic substitution): In compounds of formula VII, a divalent protecting group Y is especially an unsubstituted or mono- or di-substituted methylene group, such as 1-lower alkoxy (for example methoxy or ethoxy)-lower alkylene (for example ethylene or 1-n-butylene), e.g. —C(CH$_3$)(OC$_2$H$_5$)—, especially e.g. —C(CH$_3$)$_2$— or —CH(-phenyl)—; methylene (—CH$_2$—) is especially preferred.

In compounds of formula VIII, Q and Q' are nucleofugal leaving groups, preferably as defined above for X in compounds of formula III, especially halogen, such as bromine or iodine. Q and Q' are preferably identical.

The compound of formula VII is preferably used in a two-fold or greater, especially a 2- to 10-fold, molar excess relative to the compound of formula VIII, which yields primarily Y-protected compounds of formula I wherein $R_1$ and $R_2$ are identical. It is, however, also possible to substitute first the radical Q and then, in the monohexahydropy-rimidine intermediate that is obtainable, which can be isolated or processed further directly in situ, to react the radical Q' with a different compound of formula VII (wherein Rx and/or Y have a different meaning than in the compound of formula VII that has already been reacted). For example, it is also possible to obtain compounds of formula I wherein $R_1$ and $R_2$ are different from each other. For that purpose an excess is not absolutely necessary, that is to say each of the two compounds of formula VII can be used, for example, in a 1- to 10-fold excess, especially in a 1- to 5-fold excess, relative to the compound of formula VIII.

The reaction is carried out under the conditions customary for a nucleophilic substitution, preferably in aprotic solvents, such as ketones, for example a di-lower alkyl ketone, such as acetone, nitriles, for example a lower alkylnitrile, such as acetonitrile, carboxylic acid amides, for example a di-lower alkyl-lower alkanoylamide, such as dimethylformamide or dimethylacetamide, di-lower alkyl sulfoxides, such as dimethyl sulfoxide, in DMPU, hexamethylphosphoric acid triamide or ethers, such as di-lower alkyl ethers, for example diethyl ether, or cyclic ethers, such as tetrahydrofuran or dioxane, or also in protic solvents, such as alcohols, especially lower alkanols, for example methanol or ethanol, or mixtures of two or more of the mentioned solvents.

The starting materials of formula VII are preferably prepared by ring-closure of the corresponding N-Rx-substituted trimethylenediamines with the corresponding aldehydes or ketones suitable for the introduction of Y (such as, especially, formaldehyde or acetone), which are used for the introduction of the divalent protecting groups Y, preferably under conditions described as preferred in connection with the introduction of such protecting groups under process a), for example analogously to the process described in Okada, J., et al., Chem. Pharm. Bull. 28(11), 3310–3314 (1980).

Conversion of salts and separation of isomers

The conversion of a salt of a compound of formula I into a different salt is carded out, for example, in solvents, especially in organic solvents, more especially in polar organic solvents, very especially in esters, for example lower alkanoyl-lower alkyl esters, such as ethyl acetate, in amides, for example N,N-di-lower alkyl-lower alkanoylamides, such as dimethylformamide, in alcohols, for example hydroxy-lower alkanes, such as methanol, ethanol, ethylene glycol or glycerol, or aryl alcohols, such as phenols, for example phenol, or in dimethyl sulfoxide, in the absence or presence of water, preferably in the presence of water, or in water itself. Special preference is given to reaction in alcohols, such as the last-mentioned hydroxy-lower alkanes, in mixtures of such alcohols and water, or in water itself.

The reaction is carded out, for example, in free solution, but it may also be effected over chromatographic columns, for example by gel filtration, over ion exchangers or by means of semi-permeable membranes by osmotic processes, for example by dialysis.

The reaction is carried out at temperatures from the freezing point to the boiling point of the solutions in question, preferably at from 0° to 50° C., especially at from 20° to 40° C., for example at room temperature, in the presence or absence of a protecting gas, such as nitrogen or argon.

The compounds of formula I and the salt-forming acid are used in suitable molar ratios, or the acid is employed in excess. Preferably, the individual components are used in the molar ratio that corresponds to the ratio of the molarity of the base of formula I and the acid in the resulting salts.

The salts that are formed precipitate, for example, by themselves, in some cases only after cooling, or they are precipitated by the addition of solvents, especially of non-polar solvents, for example ethers, such as diethyl ether, or of water, and/or are obtained by partial or complete concentration by evaporation.

The reaction may also be effected via the free bases of formula I, which are prepared, for example, by converting the acid salt of a base of formula I, with a first acid, used as starting material into the free base with the aid of a base, for example a hydroxy base, such as an alkali metal hydroxide, for example NaOH or KOH, or with an OH⁻-charged ion exchanger, such as ®Amberlite-IRA-400 in the OH⁻ form, in aqueous solution in the presence or absence of an organic solvent, as defined above; the subsequent conversion of the free base is carried out, for example, as described above.

The free bases of the compounds of formula I are preferably prepared as just described, also by chromatography, for example by gel filtration, or over ion exchangers.

Mixtures of isomers obtainable according to the invention can be separated in a manner known per se into the individual isomers; diastereoisomers can be separated, for example, by partitioning between polyphasic solvent mixtures, recrystallisation and/or chromatographic separation, for example over silica gel, and racemates can be separated, for example, by the formation of salts with optically pure salt-forming reagents and separation of the mixture of diastereoisomers so obtainable, for example by means of fractional crystallisation, or by chromatography over optically active column materials.

General process conditions

The following applies in general to all processes mentioned hereinbefore and hereinafter:

Unless a specific method of synthesis is indicated for starting materials, the starting materials are known, can be prepared according to processes known per se and/or are available commercially.

In view of the close relationship between the compounds of formula I and their salts and starting materials (starting materials and intermediates) in free form and in the form of their salts, any reference hereinbefore and hereinafter to the free compounds or their salts is to be understood as meaning also the corresponding salts or free compounds, respectively, where appropriate and expedient.

All the above-mentioned process steps can be carried out under reaction conditions that are known per se, preferably those mentioned specifically, in the absence or, customarily, in the presence of solvents or diluents, preferably solvents or diluents that are inert towards the reagents used and are solvents therefor, in the absence or presence of catalysts, condensation agents or neutralising agents, for example ion exchangers, such as cation exchangers, e.g. in the H⁺ form, depending on the nature of the reaction and/or of the reactants at reduced, normal or elevated temperature, for example in a temperature range of from approximately −100° C. to approximately 190° C., preferably from approximately −80° C. to approximately 150° C., for example at from −80° to −60° C., at room temperature, at from −20° to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described under "Conversion of salts and separation of isomers".

The solvents from which those solvents that are suitable for any particular reaction may be selected include, for example, water, esters, such as lower alkyl-lower alkanoates, for example ethyl acetate, ethers, such as aliphatic ethers, for example diethyl ether, or cyclic ethers, for example tetrahydrofuran, liquid aromatic hydrocarbons, such as benzene or toluene, alcohols, such as methanol, ethanol or 1- or 2-propanol, nitriles, such as acetonitrile, halogenated hydrocarbons, such as methylene chloride, acid amides, such as dimethylformamide, bases, such as heterocyclic nitrogen bases, for example pyridine, carboxylic acid anhydrides, such as lower alkanoic acid anhydrides, for example acetic anhydride, cyclic, linear or branched hydrocarbons, such as cyclohexane, hexane or isopentane, or mixtures of those solvents, for example aqueous solutions, unless otherwise indicated in the description of the processes. Such solvent mixtures may also be used in working up, for example by chromatography or partitioning.

The compounds, including their salts, may also be obtained in the form of hydrates, or their crystals may, for example, include the solvent used for crystallisation.

If necessary, protected starting materials may be used in all process steps and the protecting groups may be removed at suitable stages of the reaction.

The invention relates also to those forms of the process in which a compound obtainable as intermediate at any stage of the process is used as starting material and the remaining process steps are carried out, or in which a starting material is formed under the reaction conditions or is used in the form of a derivative, for example in protected form or in the form of a salt, or a compound obtainable by the process according to the invention is produced under the process conditions and processed further in situ. In the process of the present invention there are preferably used those starting materials which result in the compounds of formula I described at the beginning as being especially valuable. Special preference is given to reaction conditions that are analogous to those mentioned in the Examples.

Pharmaceutical compositions and processes

The present invention relates also to pharmaceutical compositions that comprise compounds of formula I as active ingredient. Compositions for enteral, especially oral, and parenteral administration are especially preferred. The compositions comprise the active ingredient on its own or, preferably, together with a pharmaceutically acceptable carrier. The dose of active ingredient depends on the disease to be treated, and on the species, its age, weight and individual condition, and on the mode of administration.

Preference is given to a pharmaceutical composition that is suitable for administration to a warm-blooded animal, especially a human, suffering from a disorder that is responsive to a reduction in the intracellular concentrations of natural polyamines, such as especially putrescine, spermidine and spermine, especially one of the above-mentioned disorders, for example tumour disorders or protozoal infections, which composition comprises a compound of formula I or a salt thereof in an amount that is effective in the treatment of the mentioned disorders, together with at least one pharmaceutically acceptable carrier.

The pharmaceutical compositions comprise from approximately 5% to approximately 95% active ingredient, dosage forms that are in single dose form preferably comprising from approximately 20% to approximately 90% active ingredient, and dosage forms that are not in single dose form preferably comprising from approximately 5% to approximately 20% active ingredient. Unit dose forms, such as dragées, tablets or capsules, comprise from approximately 0.05 g to approximately 1.5 g of active ingredient.

The pharmaceutical compositions of the present invention are prepared for example by means of conventional mixing, granulating, confectioning, dissolving or lyophilising processes. For example, pharmaceutical compositions for oral administration can be obtained by combining the active ingredient with one or more solid carriers, optionally granulating a resulting mixture, and processing the mixture or granules, if desired and/or appropriate, by the addition of additional excipients, to form tablets or dragée cores.

Suitable carders are especially fillers, such as sugars, for example lactose, saccharose, mannitol or sorbitol, cellulose preparations and/or calcium phosphates, for example tricalcium phosphate or calcium hydrogen phosphate, and also binders, such as starches, for example corn, wheat, rice or potato starch, methylcellulose, hydroxypropylmethylcellulose, sodium carboxymethylcellulose and/or polyvinylpyrrolidone, and/or, if desired, disintegrators, such as the above-mentioned starches and also carboxymethyl starch, cross-linked polyvinylpyrrolidone, or alginic acid or a salt thereof, such as sodium alginate. Additional excipients are especially flow conditioners and lubricants, for example silicic acid, talc, stearic acid or salts thereof, such as magnesium or calcium stearate, and/or polyethylene glycol, or derivatives thereof.

Dragée cores can be provided with suitable, where appropriate enteric coatings, there being used inter alia concentrated sugar solutions, which may comprise gum arabic, talc, polyvinylpyrrolidone, polyethylene glycol and/or titanium dioxide, or coating solutions in suitable organic solvents or solvent mixtures or, for the preparation of enteric coatings, solutions of suitable cellulose preparations, such as acetylcellulose phthalate or hydroxypropylmethylcellulose phthalate. Colourings or pigments may be added to the tablets or dragée coatings, for example for identification purposes or to indicate different doses of active ingredient.

Pharmaceutical compositions for oral administration are also hard gelatin capsules, and soft sealed capsules consisting of gelatin and a plasticiser, such as glycerol or sorbitol. The hard gelatin capsules may contain the active ingredient in the form of granules, for example in admixture with fillers, such as corn starch, binders and/or glidants, such as talc or magnesium stearate, and, where appropriate, stabilisers. In soft capsules the active ingredient is preferably dissolved or suspended in suitable liquid excipients, for example aqueous solutions, fatty oils, such as sesame oil, fatty acid esters of the ethylene glycol or propylene glycol type, such as ®Lauroglycol (1,2-propylene glycol monolaurate, as a mixture of the two constitutional isomers; Gattefossé S. A., Saint Priest, France), ®Gelucire (glycerides and partial polyglycerides of fatty acids; Gattefossé S. A., Saint Priest, France) or sesame oil, paraffin oil or liquid polyethylene glycols, such as PEG 300 or 400 (Fluka, Switzerland), it likewise being possible to add stabilisers or pharmaceutically acceptable detergents.

Other oral dosage forms are, for example, syrups prepared in customary manner which comprise the active ingredient, for example, in dispersed form and in a concentration of approximately from 5% to 20%, preferably approximately 10% or in a similar concentration that provides a suitable single dose when administered, for example, in a measure of 5 or 10 ml. Also suitable are, for example, powdered or liquid concentrates for the preparation of shakes, for example in milk. Such concentrates may also be packed in single dose quantities.

Suitable rectally administrable pharmaceutical compositions are, for example, suppositories that consist of a combination of the active ingredient with a suppository base.

Suitable suppository bases are, for example, natural or synthetic triglycerides, paraffin hydrocarbons, polyethylene glycols or higher alkanols.

For parenteral administration there are suitable, especially, aqueous solutions of an active ingredient in water-soluble form, for example in the form of a water-soluble salt, or aqueous injection suspensions that comprise viscosity-increasing substances, for example sodium carboxymethylcellulose, sorbitol and/or dextran, and, if desired, stabilisers. The active ingredient, where appropriate together with excipients, can also be in the form of a lyophilisate and be made into a solution prior to parenteral administration by the addition of suitable solvents.

Solutions used, for example, for parenteral administration can also be used as infusion solutions.

The invention relates also to a process or a method for the treatment of the abovementioned pathological conditions, especially those which are responsive to a reduction in the intracellular concentration of polyamines. The compounds of the present invention can be administered prophylactically or therapeutically, preferably in an amount that is effective against the mentioned disorders, to a warm-blooded animal, for example a human, requiring such treatment, the compounds preferably being used in the form of pharmaceutical compositions. For a body weight of approximately 70 kg, a daily dose of from 1 mg to 8000 mg, for example from approximately 0.1 g to approximately 7 g, preferably from approximately 0.5 g to approximately 5 g, of a compound of the present invention is administered.

The Examples which follow serve to illustrate the invention, but they do not limit the scope thereof in any way.

Temperatures are given in degrees Celsius (°C). Where no temperature is given, the reaction is carried out at room temperature. The $R_f$ values, which indicate the relationship between the seepage propagation of the substance in question and the seepage propagation of the eluant front, are determined on thin-layer silica gel plates by thin-layer chromatography (TLC).

The ratio of solvents and eluants to one another is always given in parts by volume, unless indicated otherwise.

The other short names and abbreviations used have the following meanings:

| BOC | tert-butoxycarbonyl |
|-----|---------------------|
| DMF | dimethylformamide |
| h | hour(s) |
| min. | minute(s) |
| THF | tetrahydrofuran |

The values for proton nuclear resonance spectroscopy ($^1$H-NMR) are given in ppm (parts per million) based on tetramethylsilane as internal standard. s=singlet, d=doublet, t=triplet, q=quartet, m=multiplet, dd=double doublet.

EXAMPLE 1

(E)-1,14Di-propyl-1,5,10,14-tetraazatetradec-7-ene tetrahydrochloride

A mixture of 1.26 g (1.84 mmol) of (E)-1,14-di-propyl-1,5,10,14-tetra-BOC-1,5,10,14-tetraazatetradec-7-ene and 19 ml of 3N methanolic hydrochloric acid is stirred for 15 h at room temperature. The reaction mixture is then diluted with 19 ml of diethyl ether, the mixture is filtered, and the filtration residue is washed with diethyl ether. Drying under a high vacuum at 100° C. yields the crystalline title compound (m.p. >260° C.). $^1$H-NMR (D$_2$O): δ0.95(t,6H); 1.62–1.75(m,4H); 2.05–2.16(m,4H); 3.02(t,4H); 3.11–3.18 (m,8H); 3.76(d,4H); 6.04–6.06(m,2H).

The starting materials are prepared as follows:

a) (E)-1,14-Di-propyl-1,5,10, 14-tetra-BOC-1,5,10,14-tetraazatetradec-7-ene and (E)-1-propyl-1,5,10,14-tetra-BOC-1,5,10,14-tetraazatetradec-7-ene 0.22 g (5.5 mmol) of sodium hydride dispersion (approx. 60%) is added, with stirring, to a solution of 1.5 g (2.5 mmol) of (E)-1,5,10,14-tetra-BOC-1,5,10,14-tetraazatetradec-7-ene in 20 ml of DMF. The mixture is stirred for 1 h at room temperature and is cooled to 10° C.; 0.5 ml (5.5 mmol) of propyl bromide is added, and the reaction mixture is stirred for a further 20 h at room temperature and is then concentrated by evaporation in vacuo. The residue is partitioned between ethyl acetate and water, and the ethyl acetate phase is washed with water and brine, is dried over sodium sulfate and is concentrated by evaporation in vacuo. The resinous residue is purified by flash chromatography over silica gel having a particle size of 0.04–0.063 mm, using ethyl acetate-hexane (1:3). The product-containing fractions are concentrated by evaporation, yielding the 1,14-dipropyl title compound, $R_f$ value=0.57 (silica gel/ethyl acetate:hexane (1:1)) and the 1-propyl title compound, $R_f$ value=0.46 (silica gel/ethyl acetate:hexane (1:1)) in the form of colourless resins.

b) (E)-1,14-Di-propyl-1,5,10,14-tetra-BOC-1,5,10,14-tetraazatetradec-7-ene can also be obtained as follows:

0.4 g (10 mmol) of sodium hydride dispersion (approx. 60%) is added, with stirring, to a solution of 1.5 g (2.5 mmol) of (E)-1,5,10,14-tetra-BOC-1,5,10,14-tetraazatetradec-7-ene in 20 ml of DMF. The mixture is stirred for 15 min. at room temperature, and then 0.91 ml (10 mmol) of propyl bromide is added to the reaction mixture and stirring is continued for 41 h at room temperature. Working up analogously to 1a) yields the title compound in the form of a colourless resin, $R_f$ value=0.57 (silica gel/ethyl acetate:hexane (1:1)).

c) (E)-1,5,10,14-tetra-BOC-1,5,10,14-tetraazatetradec-7-ene

A solution of 25.86 g (105 mmol) of 2-(BOC-oxyimino)-2-phenylacetonitrile (Fluka, Switzerland) in 70 ml of THF is added dropwise over a period of 2 h, with stirring, to a solution, cooled to 5° C., of 5.01 g (25 mmol) of (E)-1,5, 10,14-tetraazatetradec-7-ene in 50 ml of THF. The reaction mixture is stirred for a further 16 h at room temperature and is then concentrated by evaporation in vacuo. The residue is purified by flash chromatography, over silica gel having an average particle size of 0.04–0.063 mm, using ethyl acetate-hexane (1:3). Concentration of the product-containing fractions by evaporation yields the resinous title compound, $R_f$ value=0.33 (silica gel/ethyl acetate:hexane (1:1)).

EXAMPLE 2

(E)-1,14-Di-allyl-1,5,10,14-tetraazatetradec-7-ene tetrahydrochloride

The title compound is obtained analogously to Example 1 starting from 0.81 g (1.19 mmol) of (E)-1,14-di-allyl-1,5, 10,14-tetra-BOC-1,5,10,14-tetraazatetradec-7-ene and 12 ml of 3N methanolic hydrochloric acid; m.p. >260° C. $^1$H-NMR (D$_2$O): δ2.02–2.17(m,4H); 3.12–3.19(m,8H); 3.69 (d,4H); 3.77(d,4H); 5.48–5.55(m,4H); 5.83–5.97(m,2H); 6.05–6.07(m,2H).

The starting material is prepared as follows:

a) (E)-1,14-Di-ally-1,5,10,14-tetra-BOC-1,5,10,14-tetraazatetradec-7-ene and (E)-1-allyl-1,5,10,14-tetra-BOC-1,5,10,14-tetraazatetradec-7-ene To a solution of 1.8 g (3 mmol) of (E)-1,5,10,14-tetra-BOC-1,5,10,14-tetraazatetradec-7-ene in 25 ml of DMF there are added, with stirring, 0.48 g (12 mmol) of sodium hydride dispersion (approx. 60%) and, after 15 min., 1.02 ml (12 mmol) of allyl bromide. The reaction mixture is stirred for 15 h at room temperature and for 20 h at 40° C.; a further 0.24 g (6 mmol) of sodium hydride dispersion (approx. 60%) and 0.51 ml (6 mmol) of allyl bromide are added at 25° C. and the reaction mixture is stirred for a further 20 h at 40° C. and is then concentrated by evaporation in vacuo. Working up analogously to Example 1a) yields the 1,14-di-allyl title compound, $R_f$ value=0.57 (silica gel/ethyl acetate:hexane (1:1)), and the 1-allyl title compound, $R_f$ value=0.46 (silica gel/ethyl acetate:hexane (1:1)), in the form of viscous oils.

EXAMPLE 3

(E)-1,14-Di-butyl-1,5,10,14-tetraazatetradec-7-ene tetrahydrochloride

The title compound is obtained analogously to Example 1 starting from 1.56 g (2.19 mmol) of (E)-1,14-di-butyl-1,5,10,14-tetra-BOC-1,5,10,14-tetraazatetradec-7-ene and 24 ml of 3N methanolic hydrochloric acid; m.p. >260° C. $^1$H-NMR (D$_2$O): δ0.91(t,6H); 1.32–1.44(m,4H); 1.60–1.70 (m,4H); 2.05–2.16(m,4H); 3.03–3.18(m,12H) 3.77(d,4H); 6.04–6.07(m,2H).

The starting material is prepared as follows:

a) (E)-1,14-Di-butyl-1,5,10,14-tetra-BOC-1,5,10,14-tetraazatetradec-7-ene and (E)-1-butyl-1,5,10,14-tetra-BOC-1,5,10,14-tetraazatetradec-7-ene To a solution of 1.8 g (3 mmol) of (E)-1,5,10,14-tetra-BOC-1,5,10,14-tetraazatetradec-7-ene in 25 ml of DMF there are added, with stirring, 0.48 g (12 mmol) of sodium hydride dispersion (approx. 60%) and, after 5 min., 1.29 ml (12 mmol) of butyl bromide. The reaction mixture is stirred for 60 h at room temperature; a further 0.24 g (6 mmol) of sodium hydride dispersion (approx. 60%) and 0.645 ml (6 mmol) of butyl bromide are added, and the mixture is stirred for a further 24 h at room temperature and is then concentrated by evaporation in vacuo. Working up analogously to Example 1a) yields the 1,4-di-butyl title compound, $R_f$ value=0.62 (silica gel/ethyl acetate:hexane ( 1:1)), and the 1-butyl title compound, $R_f$ value=0.49 (silica gel/ethyl acetate:hexane (1:1)), in the form of colourless oils.

EXAMPLE 4

(E)-1,14-Di-propargyl-1,5,10,14-tetraazatetradec-7-ene tetrahydrochloride 0.97 g (1.43 mmol) of (E)-1,14-di-propargyl-1,5,10,14-tetra-BOC-1,5,10,14-tetraazatetradec-7-ene and 15 ml of 3N methanolic hydrochloric acid are reacted analogously to Example 1. Recrystallisation of the crude product from methanol/water yields the title compound, m.p. >260° C. $^1$H-NMR (D$_2$O): δ2.07–2.19(m,4H); 3.01(t,2H); 3.15–3.30 (m,8H); 3.77(d,4H); 3.96(d,4H); 6.05–6.07(m,2H).

The starting material is prepared as follows:

a) (E)-1,14-Di-propargyl-1,5,10,14-tetra-BOC-1,5,10,14-tetraazatetradec-7-ene and (E)-1-propargyl-1,5,10,14-tetra-BOC-1,5,10,14-tetraazatetradec-7-ene To a solution of 1.8 g (3 mmol) of (E)-1,5,10,14-tetra-BOC-1,5,10,14-tetraazatetradec-7-ene in 25 ml of DMF there are added, with stirring, 0.48 g (12 mmol) of sodium hydride dispersion (approx. 60%) and, after 10 min., 0.9 ml (12 mmol) of propargyl bromide. The reaction mixture is stirred for 15 h at room temperature; a further 0.24 g (6 mmol) of sodium hydride dispersion (approx. 60%) and 0.45 ml (6 mmol) of propargyl bromide are added, and the mixture is stirred for a further 15 h at room temperature and is then concentrated by evaporation in vacuo. Working up analogously to Example 1a) yields the resinous 1,4-di-propargyl title compound, $R_f$ value=0.55 (silica gel/ethyl acetate:hexane (1:1)), and the resinous 1-propargyl title compound, $R_f$ value=0.44 (silica gel/ethyl acetate:hexane (1:1)).

EXAMPLE 5

(E)-1,14-Di-ethyl-1,5,10,14-tetraazatetradec-7-ene tetrahydrochloride 1.97 g (3 mmol) of (E)-1,14-di-ethyl-1,5,10,14-tetra-BOC-1,5,10,14-tetraazatetradec-7-ene and 30 ml of 3N methanolic hydrochloric acid are reacted analogously to Example 1. The addition of 50 ml of diethyl ether to the reaction mixture and subsequent filtration yield the title compound, m.p. >260° C. $^1$H-NMR (D$_2$O): δ1.28(t,6H); 2.04–2.15(m,4H); 3.08–3.19(m,12H); 3.76(d,4H); 6.04–6.07(m,2H).

The starting material is prepared as follows:

a) (E)-1,14-Di-ethyl-1,5,10,14-tetra-BOC-1,5,10,14-tetraazatetradec-7-ene and (E)-1-ethyl-1,5,10,14-tetra-BOC-1,5,10,14-tetraazatetradec-7-ene 0.62 g (15.5 mmol) of sodium hydride dispersion (approx. 60%) is added, with stirring, to a solution of 4.22 g (7.02 mmol) of (E)-1,5,10,14-tetra-BOC-1,5,10,14-tetraazatetradec-7-ene in 50 ml of DMF. The mixture is stirred for 15 min. at room temperature, 0.576 ml (7.72 mmol) of ethyl bromide are added, and the reaction mixture is stirred for a further 15 h at room temperature and is then concentrated by evaporation in vacuo. The residue is partitioned between ethyl acetate and water, and the ethyl acetate phase is washed with water and brine, is dried over sodium sulfate and is concentrated by evaporation in vacuo. The oily residue is purified by means of flash chromatography over silica gel having a particle size of 0.04–0.063 ram, using ethyl acetate-hexane mixtures (1:4 and 1:3). The product-containing fractions are concentrated by evaporation, yielding the 1,14-di-ethyl title compound, $R_f$ value=0.50 (silica gel/ethyl acetate:hexane (1:1)), and the 1-ethyl title compound, $R_f$ value=0.42 (silica gel/ethyl acetate:hexane (1:1)), in the form of oils.

EXAMPLE 6

(E)-1-Ally-14-ethyl-1,5,10,14-tetraazatetradec-7-ene tetrahydrochloride

A mixture of 0.28 g (0.418 mmol) of (E)-1-allyl-14-ethyl-1,5,10,14-tetra-BOC-1,5,10,14-tetraazatetradec-7-ene and 6 ml of 3N methanolic hydrochloric acid is stirred for 6 h at room temperature, and then 10 ml of diethyl ether are added. Working up analogously to Example 1 yields the title compound, m.p. >260° C. $^1$H-NMR (D$_2$O): δ1.28(t,3H); 2.05–2.17(m,4H); 3.07–3.19(m,10H); 3.69(d,2H); 3.77(d, 4H); 5.49–5.55(m,2H); 5.84–5.98(m,1H); 6.04–6.07(m,2H).

The starting material is prepared as follows:

a) (E)-1-Allyl-14-ethyl-1,5,10,14-tetra-BOC-1,5,10,14-tetraazatetradec-7-ene

To a solution of 0.272 g (0.424 mmol) of (E)-1-allyl-1,5,10,14-tetra-BOC-1,5,10,14-tetraazatetradec-7-ene (see Example 2a) in 4 ml of DMF there are added, with stirring, 0.034 g (0.85 mmol) of sodium hydride dispersion (approx. 60%) and, after 5 min., 0.069 ml (0.85 mmol) of ethyl iodide. The reaction mixture is stirred for 15 h at room temperature; a further 0.017 g (0.425 mmol) of sodium hydride dispersion (approx. 60%) and 0.034 ml (0.421 mmol) of ethyl iodide are added, and the mixture is stirred for a further 96 h at 20° C. and is then concentrated by evaporation in vacuo. Working up analogously to Example 1a), but using ethyl acetate-hexane (1:2) in the flash chromatography, yields the title compound, $R_f$ value=0.53 (silica gel/ethyl acetate:hexane ( 1:1)).

EXAMPLE 7

(E)-1-Ethyl-14-methyl-1,5,10,14-tetraazatetradec-7-ene tetrahydrochloride

A mixture of 0.32 g (0.498 mmol) of (E)-1-ethyl-14-methyl-1,5,10,14-tetra-BOC-1,5,10,14-tetraazatetradec-7-ene and 6 ml of 3N methanolic hydrochloric acid is stirred for 15 h at room temperature, and then 10 ml of diethyl ether are added. Working up analogously to Example 1 yields the title compound, m.p. >260° C. $^1$H-NMR (D$_2$O): δ1.28(t,3H); 2.03–2.17(m,4H); 2.74(s,3H); 3.07–3.19(m,10H); 3.77(d, 4H); 6.04–6.07(m,2H).

The starting material is prepared as follows:
a) (E)-1-Ethyl-14-methyl-1,5,10,14-tetra-BOC-1,5,10,14-tetraazatetradec-7-ene To a solution of 0.46 g (0.73 mmol) of (E)-1-ethyl-1,5,10,14-tetra-BOC-1,5,10,14-tetraazatetradec-7-ene (see Example 5a) in 6 ml of DMF there are added, with stirring, 0.059 g (1.47 mmol) of sodium hydride dispersion (approx. 60% ) and, after 5 min., 0.092 ml (1.47 mmol) of methyl iodide. The reaction mixture is stirred for 15 h at room temperature; a further 0.029 g (0.725 mmol) of sodium hydride dispersion (approx. 60%) and 0.045 ml (0.721 mmol) of methyl iodide are added, and the mixture is stirred for a further 96 h at 20° C. and is then concentrated by evaporation in vacuo. Working up analogously to Example 1a), but using ethyl acetate-hexane (1:2) in the flash chromatography, yields the title compound, $R_f$ value=0.42 (silica gel/ethyl acetate:hexane (1:1)).

EXAMPLE 8

(E)-1-Butyl-14-ethyl-1,5,10,14-tetraazatetradec-7-ene tetrahydrochloride

A mixture of 0.3 g (0.438 mmol) of (E)-1-butyl-14-ethyl-1,5,10,14-tetra-BOC-1,5,10,14-tetraazatetradec-7-ene and 6 ml of 3N methanolic hydrochloric acid is stirred for 15 h at room temperature, and then 10 ml of diethyl ether are added. Working up analogously to Example 1 yields the title compound, m.p. >260° C. $^1$H-NMR (D$_2$O): δ0.91 (t,3H); 1.27(t, 3H); 1.32–1.45(m,2H); 2.05–2.16(m,4H); 3.03–3.19 (m,12H); 3.77(d,4H); 6.04–6.07(m,2H).

The starting material is prepared as follows:
a) (E)-1-Butyl-14-ethyl-1,5,10,14-tetra-BOC-1,5,10,14-tetraazatetradec-7-ene 0.059 g (1.47 mmol) of sodium hydride dispersion (approx. 60%) is added, with stirring, to a solution of 0.46 g (0.73 retool) of (E)-1-ethyl-1,5,10,14-tetra-BOC-1,5,10,14-tetraazatetradec-7-ene (see Example 5a) in 6 ml of DMF. The mixture is stirred for 5 min. at room temperature; 0.159 ml (1.47 mmol) of butyl bromide is added, and the reaction mixture is stirred for a further 15 h at 20° C. and is then concentrated by evaporation in vacuo. Working up analogously to Example 1a) yields the title compound, $R_f$ value= 0.56 (silica gel/ethyl acetate:hexane ( 1:1)).

EXAMPLE 9

(E)-1-Ethyl-14-propyl-1,5,10,14-tetraazatetradec-7-ene tetrahydrochloride

A mixture of 0.5 g (0.745 mmol) of (E)-1-ethyl-14-propyl-1,5,10,14-tetra-BOC-1,5,10,14-tetraazatetradec-7-ene and 10 ml of 3N methanolic hydrochloric acid is stirred for 15 h at room temperature, and then 20 ml of diethyl ether are added. Working up analogously to Example 1 yields the title compound, m.p. >260° C. $^1$H-NMR (D$_2$O): δ0.96(t,3H); 1.28(t,3H); 1.63–1.76(m,2H); 2.05–2.16(m,4H); 2.97–3.18 (m,12H); 3.77(d,4H); 6.05–6.07(m,2H).

The starting material is prepared as follows:
a) (E)-1-Ethyl-14-propyl-1,5,10,14-tetra-BOC-1,5,10,14-tetraazatetradec-7-ene 0.05 g (1.25 mmol) of sodium hydride dispersion (approx. 60%) is added, with stirring, to a solution of 0.40 g (0.622 mmol) of (E)-1-propyl-1,5,10,14-tetra-BOC-1,5,10,14-tetraazatetradec-7-ene (see Example 1a) in 6 ml of DMF. The mixture is stirred for 5 min. at room temperature; 0.093 ml (1.25 mmol) of ethyl bromide is added, and the reaction mixture is stirred for a further 36 h at 20° C. and is then concentrated by evaporation in vacuo. Working up analogously to Example 1a) yields the title compound, $R_f$ value= 0.55 (silica gel/ethyl acetate:hexane ( 1:1)).

EXAMPLE 10

(E)-1,14-Di-ethyl-1,5,10,14-tetraazatetradec-7 -ene tetrahydrobromide and (E)-1,14-di-ethyl1-1,5,10,14-tetraazatetradec-7-ene tetrahydrochloride A mixture of 2.8 g (3.2 mmol) of (E)-1,14-di-ethyl-1,5,10,14-tetratosyl-1,5,10,14-tetraazatetradec-7-ene, 2.8 g (29.75 mmol) of phenol and 18.2 ml of an approximately 33% solution of hydrogen bromide in glacial acetic acid is heated for 8 h under reflux. The mixture is then cooled in an ice-bath and is filtered, and the resulting crystallisate is washed with ethanol/diethyl ether (1:1) and diethyl ether. The title compound (tetrahydrobromide) obtained after drying under a high vacuum at 70° C. melts at >260° C. $^1$H-NMR (D$_2$O): δ1.23(t,6H); 1.98–2.14(m,4H); 3.02–3.16 (m,12H); 3.73(d,4H); 6.01–6.04(m,2H).

For conversion into the tetrahydrochloride, 0.91 g (1.57 mmol) of (E)-1,14-di-ethyl-1,5,10,14-tetraazatetradec-7-ene tetrahydrobromide is dissolved in 2 ml of water and chromatographed over a column charged with ®Amberlite-IRA-400 ion exchanger (OH⁻ form; strongly basic ion exchanger based on a styrene/divinylbenzene polymer having a quaternary ammonium function), using water as eluant. The combined product-containing fractions are acidified to a pH of about 2 with 2N hydrochloric acid and are concentrated by evaporation in vacuo. Recrystallisation of the residue from ethanol/water yields the title compound (tetrahydrochloride), m.p. >260° C. $^1$H-NMR (D$_2$O): δ1.26 (t,6H); 2.05–2.14(m,4H); 3.06–3.17(m,12H); 3.76(d,4H); 6.04–6.06(m,2H).

The starting materials are prepared as follows:
a) (E)-1,14-Di-ethyl-1,5,10,14-tetratosyl-1,5,10,14-tetraazatetradec-7-ene and (E)-1-ethyl-1,5,10,14-tetratosyl-1,5,10,14-tetraazatetradec-7-ene 25.4 g (0.1838 mol) of potassium carbonate (anhydrous) and 7.1 ml (0.0951 mol) of ethyl bromide are added, with stirring, to a solution of 30 g (0.0367 mmol) of (E)-1,5,10,14-tetratosyl-1,5,10,14-tetraazatetradec-7-ene in 100 ml of DMF. The reaction mixture is stirred for 22 h at 70° C., and then a further 2.36 ml (0.0316 mol) of ethyl bromide are added and the mixture is stirred for a further 12 h at 70° C. The reaction mixture is cooled to room temperature and is filtered, and the filtrate is concentrated by evaporation in vacuo. The residue is purified by means of flash chromatography twice over silica gel having a particle size of 0.04–0.063 mm, using toluene-ethyl acetate (10:1 and 5:1 ) and ethyl acetate-hexane (1:1), yielding the oily 1,14-diethyl title compound, $R_f$ value=0.75 (silica gel/methylene chloride:methanol (50:1)), and the oily 1-ethyl title compound, $R_f$ value=0.65 (silica gel/methylene chloride:methanol (50:1)).

b) (E)-1,5,10,14-tetratosyl-1,5,10,14-tetraazatetradec-7-ene

A solution of 38.13 g (0.2 mol) of p-toluenesulfonic acid chloride in 300 ml of methylene chloride is added dropwise at room temperature, with stirring and under a nitrogen atmosphere, to a solution of 10.02 g (0.05 mol) of (E)-1,5,10,14-tetraazatetradec-7-ene in 100 ml (0.2 mol) of 2N sodium hydroxide solution. The reaction mixture is stirred for a further 2 h at room temperature, and then the organic phase is separated off and the aqueous phase is extracted with methylene chloride. The organic phases are combined, washed with water, dried over sodium sulfate and concentrated by evaporation. The residue is purified by means of flash chromatography over silica gel having a particle size of 0.04–0.063 mm, using ethyl acetate-hexane (1:1). Concentration of the product-containing fractions by evaporation yields the title compound in the form of an amorphous residue, $R_f$ value=0.51 (silica gel/methylene chloride:methanol (50:1)).

EXAMPLE 11

(E)-1,14-Di-ethyl-1,5,10,14-tetraazatetradec-7-ene tetrahydrochloride

A mixture of 0.18 g (0.642 mmol) of (E)-1,4-bis(3-ethyl-hexahydropyrimidin-1-yl)but-2-ene, 2.5 ml of methanol and 2.56 ml (5.12 mmol) of 2N hydrochloric acid is heated for 72 h under reflux. The reaction mixture is then cooled to room temperature, and 10 ml of methanol are added, whereupon the title compound precipitates in crystalline form. The crystallisate, which is washed with methanol and diethyl ether and dried under a high vacuum at 120° C., melts at >260° C. $^1$H-NMR (D$_2$O): δ1.27(t,6H); 2.04–2.15(m,4H); 3.07–3.18(m,12H); 3.77(d,4H); 6.04–6.06(m,2H).

The starting material is prepared as follows:

a) (E)-1,4-Bis(3-ethyl-hexahydropyrimidin-1-yl)but-2-ene

A mixture of 1.07 g (9.37 mmol) of 1-ethyl-hexahydropyrimidine (Chem. Pharm. Bull. 28, 3310 (1980)), 0.5 g (2.34 mmol) of trans-1,4-dibromo-2-butene and 10 ml of acetonitrile is heated for 16 h at 80° C., with stirring and under a nitrogen atmosphere, and is then concentrated by evaporation in vacuo. The residue is partitioned between 2N sodium hydroxide solution and methylene chloride, and the methylene chloride phase is washed with brine, dried over sodium sulfate and concentrated by evaporation in vacuo. The residue is purified by means of flash chromatography over silica gel having a particle size of 0.04–0.063 mm, using methylene chloride-methanol (9:1) and methylene chloridemethanol-concentrated ammonia (90:10:0.5), yielding the title compound in the form of an oil, $R_f$ value=0.63 (silica gel/methylene chloride:methanol:concentrated ammonia (40:10:1)).

EXAMPLE 12

(E)-1-Allyl-14-propargyl-1,5,10,14-tetraazatetradec-7-ene tetrahydrochloride

A mixture of 0.22 g (0.324 mmol) of (E)-1-allyl-14-propargyl-1,5,10,14-tetra-BOC-1,5,10,14-tetraazatetradec-7-ene and 3.3 ml of 3N methanolic hydrochloric acid is reacted analogously to Example 8. The resulting title compound melts at >260° C. $^1$H-NMR (D$_2$O): δ2.07–2.19(m, 4H); 3.02(t,1H); 3.08–3.34(m,8H); 3.69(d,2H); 3.77(d,4H); 3.96(d,2H); 5.48–5.55(m,2H); 5.84–5.97(m,1H); 6.04–6.07 (m,2H).

The starting material is prepared as follows:

a) (E)-1-Allyl-14-propargyl-1,5,10,14-tetra-BOC-1,5,10,14-tetraazatetradec-7-ene To a solution of 0.6 g (0.936 mmol) of (E)-1-allyl-1,5, 10,14-tetra-BOC- 1,5,10,14-tetraazatetradec-7-ene (see Example 2a) in 8 ml of DMF there are added, with stirring, 0.075 g (1.875 mmol) of sodium hydride dispersion (approx. 60%) and, after 5 min., 0.141 ml (1.872 mmol) of propargyl bromide. The reaction mixture is stirred for 15 h at room temperature; a further 0.0375 g (0.937 mmol) of sodium hydride dispersion (approx. 60%) and 0.071 ml (0.94 mmol) of propargyl bromide are added, and the mixture is stirred for a further 96 h at 20° C. and is then concentrated by evaporation in vacuo. Working up analogously to Example 1a) yields the title compound, $R_f$ value=0.44 (silica gel/ethyl acetate:hexane (2:3)).

EXAMPLE 13

(E)-1-Allyl-14-propyl-1,5,10,14-tetraazatetradec-7-ene tetrahydrochloride

A mixture of 0.55 g (0.805 mmol) of (E)-1-allyl-14-propyl-1,5,10,14-tetra-BOC-1,5,10,14-tetraazatetradec-7-ene and 8.2 ml of 3N methanolic hydrochloric acid is reacted analogously to Example 8. The resulting title compound melts at >260° C. $^1$H-NMR (D$_2$O): δ0.97(t,3H); 1.63–1.76 (m,2H); 2.05–2.16(m,4H); 3.02(t,2H); 3.11–3.19(m,8H); 3.69(d,2H); 3.77(d,4H); 5.48–5.55(m,2H); 5.83–5.98(m, 1H); 6.04–6.07(m,2H).

The starting material is prepared as follows:

a) (E)-1-Allyl-14-propyl-1,5,10,14-tetra-BOC-1,5,10,14-tetraazatetradec-7-ene

To a solution of 0.7 g (1.092 mmol) of (E)-1-allyl-1,5, 10,14-tetra-BOC-1,5,10,14-tetraazatetradec-7-ene (see Example 2a) in 9.4 ml of DMF there are added, with stirring, 0.087 g (2.175 mmol) of sodium hydride dispersion (approx. 60%) and, after 5 min., 0.212 ml (2.176 mmol) of propyl iodide. The reaction mixture is stirred for 15 h at room temperature; a further 0.043 g (1.075 mmol) of sodium hydride dispersion (approx. 60%) and 0.106 ml (1.088 mmol) of propyl iodide are added, and the mixture is stirred for a further 96 h at 20° C. and is then concentrated by evaporation in vacuo. Working up analogously to Example 1a) yields the oily title compound, $R_f$ value=0.46 (silica gel/ethyl acetate:hexane (2:3)).

EXAMPLE 4

(E)-1-Allyl-14-methyl-1,5,10,14-tetraazatetradec-7-ene tetrahydrochloride

A mixture of 0.6 g (0.916 mmol) of (E)-1-allyl-14-methyl-1,5,10,14-tetra-BOC-1,5,10,14-tetraazatetradec-7-ene and 9 ml of 3N methanolic hydrochloric acid is reacted analogously to Example 8. The resulting title compound melts at >260° C. ¹H-NMR (D₂O): δ2.07–2.17(m,4H); 2.73(s,3H); 3.12–3.19(m,8H); 3.69(d,2H); 3.77(d,4H); 5.48–5.55(m,2H); 5.83–5.98(m, 1H); 6.04–6.07 (m,2H).

The starting material is prepared as follows:

a) (E)-1-Allyl-14-methyl-1,5,10,14-tetra-BOC-1,5,10,14-tetraazatetradec-7-ene

To a solution of 0.6 g (0.936 mmol) of (E)-1-allyl-1,5,10,14-tetra-BOC-1,5,10,14-tetraazatetradec-7-ene (see Example 2a) in 8 ml of DMF there are added, with stirring, 0.075 g (1.875 mmol) of sodium hydride dispersion (approx. 60%) and, after 5 min., 0.117 ml (1.875 mmol) of methyl iodide. The reaction mixture is stirred for 15 h at room temperature; a further 0.075 g (1.875 mmol) of sodium hydride dispersion (approx. 60%) and 0.117 ml (1.875 mmol) of methyl iodide are added, and the mixture is stirred for a further 96 h at 20° C. and is then concentrated by evaporation in vacuo. Working up analogously to Example 1a, but using ethyl acetate-hexane (1:2) in the flash chromatography, yields the title compound, $R_f$ value=0.36 (silica gel/ethyl acetate:hexane (2:3)).

EXAMPLE 15

(E)-1-Isopropyl-14-propyl-1,5,10,14-tetraazatetradec-7-ene tetrahydrochloride

A mixture of 0.24 g (0.35 mmol) of (E)-1-isopropyl-14-propyl-1,5,10,14-tetra-BOC-1,5,10,14-tetraazatetradec-7-ene and 4 ml of 3N methanolic hydrochloric acid is stirred for 4 h at room temperature. Then the reaction mixture is diluted with 6 ml of diethyl ether and is worked up analogously to Example 1. The resulting title compound melts at >260° C. ¹H-NMR (D₂O): δ0.97(t,3H); 1.32(d,6H); 1.63–1.76(m,2H); 2.04–2.17(m,4H); 3.02(t,2H); 3.12–3.19 (m,8H); 3.37–3.49(m,1H); 3.78(d,4H); 6.05–6.07(m,2H).

The starting materials are prepared as follows:

a) (E)-1-Isopropyl-14-propyl-1,5,10,14-tetra-BOC-1,5,10,14-tetraazatetradec-7-ene 0.042 g (1.05 mmol) of sodium hydride dispersion (approx. 60%) is added, with stirring, to a solution of 0.338 g (0.526 mmol) of (E)-1-isopropyl-1,5,10,14-tetra-BOC-1,5,10,14-tetraazatetradec-7-ene in 5 ml of DMF. The mixture is stirred for 5 min. at room temperature; 0.103 ml (1.05 mmol) of propyl iodide is added, and the reaction mixture is stirred for a further 16 h at 20° C. and is then concentrated by evaporation in vacuo. Working up analogously to Example 1a), using ethyl acetate-hexane (1:3) and ethyl acetate-hexane (1:2) in the flash chromatography, yields the title compound, $R_f$ value=0.51 (silica gel/ethyl acetate:hexane (2:3)).

b) (E)-1-Isopropyl-1,5,10,14-tetra-BOC-1,5,10,14-tetraazatetradec-7-ene

To a solution of 1.5 g (2.5 mmol) of (E)-1,5,10,14-tetra-BOC-1,5,10,14-tetraazatetradec7-ene in 20 ml of DMF there are added, with stirring, 0.4 g (10 mmol) of sodium hydride dispersion (approx. 60%) and, after 15 min., 1 ml (10 mmol) of isopropyl iodide. The reaction mixture is stirred for 16 h at room temperature; a further 0.4 g ( 10 mmol) of sodium hydride dispersion (approx. 60%) and 1 ml (10 mmol) of isopropyl iodide are added, and the mixture is stirred for a further 24 h at 20° C. and for 24 h at 50° C. and is then concentrated by evaporation in vacuo. Working up analogously to Example 1a), using ethyl acetate-hexane (1:3) and ethyl acetate-hexane (1:2) in the flash chromatography, yields the title compound, $R_f$ value=0.37 (silica gel/ethyl acetate:hexane (2:3)).

EXAMPLE 16

(E)-1,14-Di-cyclopropylmethyl-1,5,10,14-tetraazatetradec-7-ene tetrahydrochloride A mixture of 1.5 g (2.116 mmol) of (E)-1,14-di-cyclopropylmethyl-1,5,10,14-tetra-BOC-1,5,10,14-tetraazatetradec-7-ene and 23 ml of 3N methanolic hydrochloric acid is stirred for 5 h at room temperature, and then 20 ml of diethyl ether are added. Working up analogously to Example 1 yields the title compound, m.p. >260° C. ¹H-NMR (D₂O): δ0.33–0.38(m,4H); 0.65–0.71 (m,4H); 1.00–1.14(m,2H); 2.05–2.16(m,4H); 2.96(d,4H); 3.13–3.19 (m,8H); 3.77(d,4H); 6.04–6.07(m,2H).

The starting material is prepared as follows:

a) (E)-1,14-Di-cyclopropylmethyl-1,5,10,14-tetra-BOC-1,5,10,14-tetraazatetradec-7-ene 0.4 g (10 mmol) of sodium hydride dispersion (approx. 60%) is added, with stirring, to a solution of 1.5 g (2.5 mmol) of (E)-1,5,10,14-tetra-BOC-1,5,10,14-tetraazatetradec-7-ene in 21.5 ml of DMF. The mixture is stirred for 15 min. at room temperature; then 1.06 ml (10 mmol) of bromomethyl-cyclopropane (approx. 90% ) are added to the reaction mixture and stirring is continued for 90 h at room temperature. Working up analogously to Example 1a) yields the title compound in the form of a colourless resin, $R_f$ value=0.47 (silica gel/ethyl acetate:hexane (2:3)).

EXAMPLE 17

(E)-1,14-Di-propyl-1,5,10,14-tetraazatetradec-7-ene tetrahydrochloride

A mixture of 0.265 g (0.859 mmol) of (E)-1,4-bis(3-propylhexahydro-pyrimidin-1-yl)but-2-ene, 3 ml of methanol and 3.4 ml (6.8 mmol) of 2N hydrochloric acid is heated for 19 h under reflux and is then concentrated by evaporation in vacuo. Recrystallisation of the residue from methanol/water yields the title compound, m.p. >260° C. ¹H-NMR (D₂O): δ0.96(t,6H); 1.62–1.76(m,4H); 2.05–2.16(m,4H); 3.02(t,4H); 3.11–3.18(m,8H); 3.77(d,4H); 6.03–6.06(m, 2H).

The starting materials are prepared as follows:

a) (E)-1,4-Bis(3-propylhexahydro-pyrimidin-1-yl)but-2-ene

A mixture of 0.68 g (17.9 mmol) of lithium aluminium hydride, 10 ml of dioxane and 1 g (2.97 mmol) of (E)-1,4-bis(3-propionylhexahydro-pyrimidin-1-yl)but-2-ene is stirred for 15 h at 100° C., with stirring and under a nitrogen atmosphere. After cooling to 5° C. in an ice-bath, there are added dropwise to the reaction mixture, in succession, a mixture of 0.53 ml of water and 2 ml of tetrahydrofuran, 0.53 ml of 1N sodium hydroxide solution and 1.1 ml of water, care being taken to ensure that the temperature does not exceed 15° C. The mixture is stirred for a further 1 h at room temperature and is filtered, the filtration residue is washed with tetrahydrofuran, and the filtrate is then concentrated by evaporation in vacuo. The oily residue is purified by means of flash chromatography over silica gel having a particle size of 0.04–0.063 mm, using methylene chloride-methanol (10:1) and methylene chloride-methanol-concentrated ammonia (100:10:0.5). Concentration of the product-containing fractions by evaporation yields the title compound in the form of an oil, $R_f$ value=0.56 (silica gel/methylene chloride:methanol:concentrated ammonia (150:50:1)).

b) (E)-1,4-Bis(3-propionylhexahydro-pyrimidin-1-yl)but-2-ene 5 ml (38.8 mmol) of propionic acid anhydride are added at 0° C., with stirring, to a mixture of 1.77 g (7.89 mmol) of (E)-1,4-bis(hexahydro-pyrimidin-1-yl)but-2-ene and 10 ml of pyridine. The reaction mixture is stirred for a further 1 h at room temperature and is then concentrated by evaporation in vacuo. The oily residue is partitioned between 15% sodium hydroxide solution and ethyl acetate. The organic phase is washed with brine and dried over sodium sulfate and is then concentrated by evaporation in vacuo, yielding the title compound in the form of an oil, $R_f$ value=0.77 (silica gel/methylene chloride:methanol:concentrated ammonia (40:10:1)).

c) (E)-1,4-Bis(hexahydro-pyrimidin-1-yl)but-2-ene

A mixture of 7.6 ml (99.8 mmol) of formaldehyde (approx. 36.5% aqueous solution) and 10 ml of water is added dropwise over a period of 1 h, with stirring, to a solution, cooled to 0° C., of 10 g (49.9 mmol) of (E)-1,5,10,14-tetraazatetradec-7-ene in 25 ml of water. The reaction mixture is stirred for a further 2 h at 0° C. and a further 15 h at room temperature and is then concentrated by evaporation in vacuo. The residue is purified by means of flash chromatography over silica gel having a particle size of 0.04–0.063 mm, using methylene chloride-methanol-concentrated ammonia (100:10:0.5) and methylene chloride-methanol-concentrated ammonia (50:10:1). The product-containing fractions are concentrated by evaporation and the residue is sublimed under a high vacuum at 85° C. The resulting title compound melts at 125°–127° C.

EXAMPLE 18

(E)-1,14-Di-propyl-1,5,10,14-tetraazatetradec-7-ene tetrahydrochloride 0.25 g (0.0008 mol) of (E)-1,14-di-propionyl-1,5,10,14-tetraazatetradec-7-ene is added, with stirring and while cooling in an ice-bath, to a solution of 2.4 g (approx. 0.00831 mol) of sodium dihydro-bis(2-methoxyethoxy) aluminate (approx. 70% solution in toluene; Fluka, Buchs, Switzerland) in 10 ml of THF. The reaction mixture is heated for 2 h under reflux and is then cooled in an ice-bath, and 2.4 ml of 30% sodium hydroxide solution, 10 ml of THF and 3 g of anhydrous magnesium sulfate are added in succession. The mixture is filtered, the filtration residue is washed with THF, and the filtrate is concentrated by evaporation in vacuo. The oily residue is dissolved in 15 ml of ethanol, and 1 ml of 4N hydrochloric acid is added to the solution. The crystallisate that forms is filtered off and then recrystallised twice more from methanol/water. The resulting title compound melts at >260° C. $^1$H-NMR (D$_2$O): δ0.96(t,6H); 1.63–1.76(m,4H); 2.05–2.16(m,4H); 3.02(t,4H); 3.11–3.18 (m,8H); 3.77(d,4H); 6.04–6.07(m,2H).

The starting material is prepared as follows:

a) (E)-1,14-Di-propionyl-1,5,10,14-tetraazatetradec-7-ene

A mixture of 1.84 g (0.005468mmol) of (E)-1,4-bis(3-propionylhexahydro-pyrimidin-1-yl)but-2-ene (Example 17b), 44 ml of methanol, 2.74 ml (0.03405 mol) of pyridine and 4.11 g (0.03949 mol) of malonic acid is heated for 2 h under reflux and is then concentrated by evaporation in vacuo. 10 ml of 30% sodium hydroxide solution are added to the oily residue, the mixture is extracted thoroughly with ethyl acetate, the combined ethyl acetate extracts are dried over anhydrous sodium sulfate, and the resulting product is concentrated by evaporation in vacuo to a volume of about 25 ml. The crystalline precipitate that forms is filtered off and, for purification purposes, is recrystallised from acetonitrile. The resulting title compound melts at 82°–84° C.

EXAMPLE 19

(E)-1,14-Di-ethyl-1,5,10,14-tetraazatetradec-7-ene tetrahydrochloride 0.5 g (0.624 mmol) of (E)-1,14-di-ethyl-1,5,10,14-tetra-diethoxyphosphoryl-1,5,10,14-tetraazatetradec-7-ene is dissolved in 5 ml of THF; then hydrogen chloride is passed into the solution for a period of about 45 min. at 0°–5° C. and the reaction mixture is stirred for 20 h at room temperature. The addition of 15 ml of diethyl ether to the reaction mixture, filtration, washing the crystallisate with diethyl ether and drying under a high vacuum yield the title compound, m.p. >260° C. $^1$H-NMR (D$_2$O): δ1.28(t,6H); 2.05–2.16(m,4H); 3.08–3.19(m,12H); 3.77(d,4H); 6.05–6.07(m,2H).

The starting materials are prepared as follows:

a) (E)-1,14-Di-ethyl-1,5,10,14-tetra-diethoxyphosphoryl-1,5,10,14-tetraazatetradec-7-ene 0.16 g (4 mmol) of sodium hydride dispersion (approx. 60%) is added, with stirring, to a solution of 0.745 g (1 mmol) of (E)-1,5,10,14-tetra-diethoxyphosphoryl-1,5,10,14-tetraazatetradec-7-ene in 5 ml of DMF. The mixture is stirred for 10 min. at room temperature, 0.3 ml (4 mmol) of ethyl bromide are added, and the reaction mixture is stirred for a further 2 h at 20° C. and is then concentrated by evaporation in vacuo. The residue is partitioned between ethyl acetate and ice-cold water, and the ethyl acetate phase is washed with water and brine, is dried over sodium sulfate and is concentrated by evaporation in vacuo. The oily residue is purified by means of flash chromatography over silica gel having a particle size of 0.04–0.063 mm, using methylene chloride-methanol mixtures (49:1 and 9:1). Concentration of the product-containing fractions by evaporation yields the title compound in the form of a colourless oil, $R_f$ value=0.34 (silica gel, eluant methylene chloride:methanol (9:1)).

b) (E)-1,5,10,14-Tetra-diethoxyphosphoryl-1,5,10,14-tetraazatetradec-7-ene

A solution of 12.4 g (89.8 mmol) of diethyl phosphite in 18 ml of carbon tetrachloride is added dropwise at 10°–15° C., with stirring, to a mixture of 3 g (14.97 mmol) of (E)-1,5,10,14-tetraazatetradec-7-ene, 18 g (179.8 mmol)of potassium hydrogen carbonate, 24.85 g (179.8 mmol) of potassium carbonate, 1.45 g (4.5 mmol) of tetrabutylammonium bromide and 70 ml of methylene chloride. The reaction mixture is stirred for a further 90 h at room temperature and is filtered, the filtrate is washed with water, and the organic phase is dried over sodium sulfate and concentrated by evaporation in vacuo. The oily residue is purified by means of flash chromatography over silica gel having a particle size of 0.04–0.063 mm, using methylene chloride-methanol (49:1) and methylene chloridemethanol (9:1). Concentration of the product-containing fractions by evaporation yields the title compound in the form of an oil, $R_f$ value=0.28 (silica gel, eluant methylene chloride:methanol (9:1)).

EXAMPLE 20

(E)-1,14-Di-allyl-1,5,10,14-tetraazatetradec-7-ene tetrahydrochloride

For conversion into the title compound, 37.45 g of crude (E)-1,14-di-allyl-1,5,10,14-tetra(diethoxyphosphoryl)-1,5,10,14-tetraazatetradec-7-ene are dissolved in 170 ml of 7THF, and hydrogen chloride is passed into the solution at 5° C. until saturated. The reaction mixture is stirred for 15 h at room temperature, 250 ml of diethyl ether are added to the resulting suspension, the mixture is filtered and the filtration residue is washed with a small amount of ethanol and diethyl ether. Recrystallisation from ethanol/water (with treatment with activated carbon) and drying the crystallisate under a high vacuum at 120° C. yield the title compound, m.p. >260° C. $^1$H-NMR (D$_2$O): δ2.06–2.17(m,4H); 3.13–3.19(m,8H); 3.69(d,4H); 3.78(d,4H); 5.49–5.55(m, 4H); 5.84–5.98(m,2H); 6.05–6.07(m,2H).

The starting materials are prepared as follows:

a) (E)-1,5,10,14-Tetra(diethoxyphosphoryl )-1,5,10,14-tetraazatetradec-7-ene

A solution of 43.5 g (0.315 mol) of diethyl phosphite in 90 ml of carbon tetrachloride is added dropwise at 10°–15° C. over a period of 45 min., with stirring, to a mixture of 15.02 g (0.075 mol) of (E)-1,5,10,14-tetraazatetradec-7-ene, 63.08 g (0.63 mmol) of potassium hydrogen carbonate, 87.07 g (0.63 mol) of potassium carbonate, 5.093 g (0.0158 mol) of tetrabutylammonium bromide and 350 ml of methylene chloride. The reaction mixture is stirred for a further 87 h at room temperature and is then allowed to stand for 63 h at 20° C. and is filtered. The filtrate is washed with water and the organic phase is dried over sodium sulfate and is concentrated by evaporation in vacuo. The evaporation residue that is obtained is crude (E)-1,5,10,14-tetra(diethoxyphosphoryl)-1,5,10,14-tetraazatetradec-7-ene in the form of a yellow oil, R$_f$ value=0.28 (silica gel/methylene chloride:methanol (9:1)), which is used further directly.

b) (E)-1,14-Di-allyl-1,5,10,14-tetra(diethoxyphosphoryl)-1,5,10,14-tetraazatetradec-7-ene 51.3 g of crude (E)-1,5,10,14-tetra(diethoxyphosphoryl)-1,5,10,14-tetraazatetradec-7-ene are dissolved in 100 ml of DMF, and 8.27 g (0.2067 mol) of sodium hydride dispersion (approx. 60%) are added in portions to the solution, with stirring. After stirring for 15 min. at 20° C., 17.49 ml (0.2067 mol) of allyl bromide are added dropwise, and the reaction mixture is stirred for a further 15 h at room temperature and is then concentrated by evaporation in vacuo. The evaporation residue is partitioned between ethyl acetate and ice-cold water, and the organic phase is washed in succession with 20% citric acid, 2N sodium carbonate solution and brine, is dried over sodium sulfate and is concentrated by evaporation in vacuo. There is obtained as residue crude (E)-1,14-di-allyl-1,5,10,14-tetra(diethoxyphosphoryl)-1,5,10,14-tetraazatetradec-7-ene in the form of a yellow oil, R$_f$ value= 0.38 (silica gel/methylene chloride:methanol (9:1)).

EXAMPLE 21

Capsules

Capsules each comprising 1 g of active ingredient, for example one of the acid addition salts of Examples 1 to 20, can be prepared as follows:

| Composition (for 1250 capsules): | |
| --- | --- |
| active ingredient | 1250 g |
| talc | 180 g |
| wheat starch | 120 g |
| magnesium stearate | 80 g |
| lactose | 20 g |

The powdered substances are pressed through a sieve having a mesh size of 0.6 mm and mixed 1.32 g portions of the mixture are introduced into gelatin capsules by means of a capsule-filling machine.

EXAMPLE 22

Levels of Putrescine, spermidine and spermine in mouse ascites L 1210 leukemia cells:

Using the method analoguous to Porter et al. as described in detail above, the following levels of putrescine (PU), spermidine (SPD) and spermine (SPM) (given in % of the respective control without addition of a compound of formula I) are obtained when the title compound is administered in the respective concentration (μM) given in the table (48 h incubation):

| Example | % PU | % SPD | % SPM | concentration (μM) of test cpd.: |
| --- | --- | --- | --- | --- |
| 1, 17, 18 | 9.4 | 12 | 67 | 10 |
| 2, 20 | 16 | 3.1 | 36 | 10 |
| 5, 10, 11, 19 | 4.1 | 2.1 | 30 | 5 |
| 6 | 4.1 | 2.1 | 12 | 10 |
| 8 | 4.8 | 0.2 | 4.0 | 10 |
| 9 | 6.9 | 2.0 | 19 | 10 |
| 13 | 0 | 1.3 | 25 | 10 |
| 16 | 12 | 24 | 62 | 10 |

EXAMPLE 23

Inhibition of growth of human T24 bladder carcinoma cells:

Using the method for inhibition of growth of human T24 bladder carcinoma cells om Eagle's minimal essential medium (see above), the following test results are obtained (given as IC$_{50}$=concentration of the active ingredient at which the number of cells per well at the end of the incubation period is only 50% of the number of cells in the control cultures):

| Compound of Example No. | IC$_{50}$ (μM) |
| --- | --- |
| 1, 17, 18 | 0.64 |
| 2, 20 | 0.60 |
| 3 | 8.2 |
| 6 | 3 |
| 8 | 0.55 |
| 9 | 1.1 |
| 13 | 2.14 |
| 16 | 0.92 |

What is claimed is:

1. A compound of formula I,

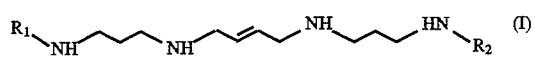

wherein R$_1$ and R$_2$, each independently of the other, are selected from C$_2$–C$_4$alkyl, C$_3$–C$_4$alkenyl wherein the double bond does not originate from the carbon atom that is bonded to a nitrogen bonding R$_1$ or R$_2$, and from C$_3$–C$_4$cycloalkylmethyl, or a salt thereof.

2. A compound according to claim 1 with the proviso that R$_1$ and R$_2$ together have not more than 6 carbon atoms.

3. A compound according to claim 1 wherein R$_1$ and R$_2$, each independently of the other, are selected from ethyl, n-propyl, n-butyl and allyl, or a salt thereof.

4. A compound according to claim 3, wherein R$_1$ and R$_2$ together have 4, 5 or 6 carbon atoms, or a salt thereof.

5. A compound according to claim 1, wherein R$_1$ is ethyl and R$_2$ is selected from ethyl, n-propyl, n-butyl and allyl, or a salt thereof.

6. A pharmaceutical composition suitable for administration to a warm-blooded animal for the treatment of proliferative disorders that are responsive to a reduction in the intracellular polyamine concentration of natural polyamines, comprising a compound of formula I according to claim 1, or a pharmaceutically acceptable salt of such a compound having at least one salt-forming group that is effective in the treatment of the mentioned disorder, together with a pharmaceutically acceptable carrier.

7. A method of treating a warm-blooded animal suffering from bladder carcinoma that is responsive to a reduction in the intracellular concentration of polyamines, which method comprises administering to the warm-blooded animal requiring such treatment a compound of formula I according to claim 1, or a pharmaceutically acceptable salt thereof, in a dose that is effective in reducing the intracellular concentration of polyamines.

8. A process for the preparation of a compound of formula I according to claim 1, which process comprises a) nucleophilically substituting an amino compound of formula II

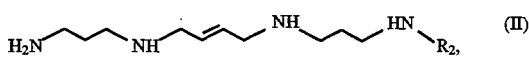

wherein $R_2$ is as defined for compounds of formula I and any functional groups that are not to take part in the reaction are, if necessary, in protected form, with a compound of formula III

wherein $R_1$ is as defined for compounds of formula I and X is a nucleofugal leaving group, and removing any protecting groups that are present, and, if desired, converting an obtainable free compound of formula I into its salt, converting an obtainable salt of a compound of formula I into the free compound or into a different salt of a compound of formula I, and/or separating obtainable mixtures of isomers into the individual isomers.

9. The compound according to claim 1, said compound being selected from the group consisting of (E)-1,14-Di-allyl-1,5,10,14-tetraazatetradec-7-ene;

(E)-1,14-Di-butyl-1,5,10,14-tetraazatetradec-7-ene of formula I;

(E)-1,14-Di-ethyl-1,5,10,14-tetraazatetradec-7-ene;

(E)-1-Allyl-14-ethyl-1,5,10,14-tetraazatetradec-7-ene;

(E)-1-Butyl-14-ethyl-1,5,10,14-tetraazatetradec-7-ene;

(E)-1-Ethyl-14-propyl-1,5,10,14-tetraazatetradec-7-ene;

(E)-1-Allyl-14-methyl-1,5,10,14-tetraazatetradec-7-ene;

(E)-1-Isopropyl-14-propyl-1,5,10,14-tetraazatetradec-7-ene;

(E)-1,14-Di-cyclopropylmethyl-1,5,10,14-tetraazatetradec-7-ene; and (E)-1,14-Di-propyl-1,5,10,14-tetraazatetradec-7-ene; or a salt thereof.

10. The compound according to claim 1, said compound being (E)-1,14-di-propyl-1,5,10,14-tetraazatetradec-7-ene, or a pharmaceutically acceptable salt thereof.

11. The compound according to claim 1, said compound being (E)-1-allyl-14-propyl-1,5,10,14-tetraazatetradec-7-ene, or a pharmaceutically acceptable salt thereof.

* * * * *